United States Patent
Maekawa et al.

(10) Patent No.: US 12,194,127 B2
(45) Date of Patent: *Jan. 14, 2025

(54) COSMETIC COMPOSITION

(71) Applicant: KAO CORPORATION, Tokyo (JP)

(72) Inventors: Tomoka Maekawa, Sumida-ku (JP); Tomoyuki Suzawa, Sumida-ku (JP); Kazutaka Ishikawa, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 10 days.

This patent is subject to a terminal disclaimer.

(21) Appl. No.: 17/999,885

(22) PCT Filed: May 27, 2021

(86) PCT No.: PCT/JP2021/020142
§ 371 (c)(1),
(2) Date: Nov. 25, 2022

(87) PCT Pub. No.: WO2021/246275
PCT Pub. Date: Dec. 9, 2021

(65) Prior Publication Data
US 2023/0320965 A1    Oct. 12, 2023

(30) Foreign Application Priority Data
Jun. 1, 2020  (JP) ................ 2020-095678

(51) Int. Cl.
*A61Q 5/10* (2006.01)
*A61K 8/58* (2006.01)
*A61K 8/898* (2006.01)

(52) U.S. Cl.
CPC .............. *A61K 8/585* (2013.01); *A61K 8/898* (2013.01); *A61Q 5/10* (2013.01)

(58) Field of Classification Search
CPC .... A61K 8/585; A61K 8/898; A61K 2800/43; A61Q 5/10; A61Q 5/06
USPC ........................................................ 8/405
See application file for complete search history.

(56) References Cited

U.S. PATENT DOCUMENTS

| | | | | |
|---|---|---|---|---|
| 6,475,500 B2* | 11/2002 | Vatter | ........... | A61Q 17/04 424/401 |
| 6,524,598 B2* | 2/2003 | Sunkel | ........... | A61Q 17/04 514/844 |
| 6,610,278 B2* | 8/2003 | Kashimoto | ........... | A61K 8/895 424/78.17 |
| 2003/0211953 A1* | 11/2003 | Glenn | ........... | A61K 8/898 8/405 |
| 2008/0184496 A1* | 8/2008 | Brun | ........... | A61K 8/893 8/405 |
| 2010/0083446 A1* | 4/2010 | Brun | ........... | A61K 8/891 8/405 |
| 2011/0318295 A1 | 12/2011 | Shimizu et al. | | |

FOREIGN PATENT DOCUMENTS

| | | | |
|---|---|---|---|
| EP | 1 356 802 A1 | 10/2003 | |
| FR | 2 958 544 A1 | 10/2011 | |
| JP | 10-101531 A | 4/1998 | |
| JP | 2005-524691 A | 8/2005 | |
| JP | 2005-527595 A | 9/2005 | |
| JP | 2008-189639 A | 8/2008 | |
| JP | 2013/43848 A | 3/2013 | |
| JP | 2013-95695 A | 5/2013 | |
| JP | 2013/209323 A | 10/2013 | |
| JP | 2013227313 A * | 11/2013 | ............ A61Q 5/12 |
| JP | 2017-109954 A | 6/2017 | |
| WO | WO 2011/136389 A2 | 11/2011 | |

OTHER PUBLICATIONS

International Search Report mailed on Aug. 3, 2021 in PCT/JP2021/020142 filed on May 27, 2021 (2 pages).
Extended European Search Report issued May 16, 2024 in European Application No. 21816653.6, 11 pgs.

* cited by examiner

*Primary Examiner* — Eisa B Elhilo
(74) *Attorney, Agent, or Firm* — Oblon, McClelland, Maier & Neustadt, L.L.P.

(57) ABSTRACT

A cosmetic composition including: (A) a silicone film-forming agent, and (B) an organopolysiloxane having a polyalkylene oxide moiety and a cationic group other than the component (A), wherein the content of water is 50% by mass or less. The cosmetic composition is a hair cosmetic composition or a hair dye composition.

14 Claims, No Drawings

COSMETIC COMPOSITION

CROSS REFERENCE TO RELATED APPLICATIONS

This application is a National Stage entry under 35 U.S.C. § 371 of PCT/JP2021/020142, filed on May 27, 2021, and claims priority to Japanese Patent Application No. 2020-095678, filed on Jun. 1, 2020. The entire contents of both are incorporated herein by reference.

FIELD OF THE INVENTION

The present invention relates to a cosmetic composition.

BACKGROUND OF THE INVENTION

A cosmetic material capable of semi-permanently improving the condition of skin or hair is desired. For example, for improving the feel of hair, it is known to use an rinse-off conditioner or an leave-on conditioner, but the effect thereof is mostly lost in one shampooing, and a product having an ability to sustain the effect is desired.

For example, Patent Literature 1 (JP 2005-524691 T) and Patent Literature 2 (JP 2005-527595 T) disclose a hair treatment composition and a fiber treatment composition, which contains a mixture of a predetermined functionalized silicone polymer and a durable additive miscible with the functionalized silicone, and which can be rapidly rinsed away so as not to lose the conditioning effect.

SUMMARY OF THE INVENTION

The present invention relates to the following [1] to [8].

[1] A cosmetic composition containing (A) a silicone film-forming agent, and (B) an organopolysiloxane having a polyalkylene oxide moiety and a cationic group other than the component (A), wherein the content of water is 50% by mass or less.

[2] The cosmetic composition according to the above [1], which is a hair cosmetic composition.

[3] The cosmetic composition according to the above [1], which is a hair dye composition.

[4] A method for treating a keratin substance, including a step of applying the cosmetic composition of the above [1] to a keratin substance and then drying it.

[5] A method for treating hair, including a step of applying the hair cosmetic composition of the above [2] to hair and then drying it.

[6] A method for dyeing hair, including a step of applying the hair dye composition of the above [3] to hair and then drying it.

[7] A leave-on cosmetic composition containing (A) a silicone film-forming agent, and (B) an organopolysiloxane having a polyalkylene oxide moiety and a cationic group other than the component (A).

[8] A cosmetic kit provided with the following compositions (I) and (II):

(I) a composition containing (A) a silicone film-forming agent, (II) a composition containing (B) an organopolysiloxane having a polyalkylene oxide moiety and a cationic group other than the component (A).

DETAILED DESCRIPTION OF THE INVENTION

Definition

"Polymer" used in the present specification means a compound corresponding to a repetition of one or plural units (these units are derived from a compound known as a monomer). This or these units are repeated at least two times preferably at least three times.

"Hair" used in the present specification means mainly head hair.

"Hydrophobic" used in the present specification means that a solubility in water of a substance is less than 1% by mass at 25° C.

"Film formation" used in the present specification means that, when applied to a substrate, a film is left thereon.

"Volatile" used in the present specification means a substance having a boiling point of 260° C. or lower under normal pressure.

Cosmetic Composition

The cosmetic composition of the present invention is a cosmetic composition containing:

(A) a silicone film-forming agent, and (B) an organopolysiloxane having a polyalkylene oxide moiety and a cationic group other than the component (A), wherein:

the content of water is 50% by mass or less.

Having the above constitution, the cosmetic composition of the present invention is, when applied to a keratin substance such as skin or hair in a dry state and especially when used without rinsing away with water, able to impart a smooth feel in a dry state or in rinsing, and is, even after rinsing, able to be excellent in sustainability of these effects. In addition, when the cosmetic composition is used as a hair dye composition, it can impart the above-mentioned effects to hair and secure good color consistency with little fading by shampooing.

Regarding the treatment compositions described in Patent Literatures 1 and 2, the publications say that the functionalized silicone polymer adheres to hair with durability, but the functionalized silicone polymer is very sticky and has a problem in that a good feel is difficult to obtain.

Further, these treatment compositions are assumed to be for so-called rinse-off use in which they are rinsed away with water after applied to hair or fibers. Therefore, in the case where the treatment compositions are used like leave-on treatment agents and are dried as such without rinsing away, a sticker feel is given that could not be able to accept for practical use.

An object of the present invention is to provide a cosmetic composition which is, when applied to a keratin substance such as skin or hair in a dry state and especially when used without rinsing away with water, able to impart a smooth feel in a dry state or in rinsing, and is, even after rinsing, able to be excellent in sustainability of these effects.

The present inventors have found that a cosmetic composition containing a silicone film-forming agent, and an organopolysiloxane having a polyalkylene oxide moiety and a cationic group other than the component (A), in which the content of water is a predetermined amount or less, can solve the above-mentioned problems, and have completed the present invention.

According to the present invention, there can be provided a cosmetic composition which is, when applied to a keratin substance such as skin or hair in a dry state and especially when used without rinsing away with water, able to impart a smooth feel in a dry state or in rinsing, and is, even after rinsing, able to be excellent in sustainability of these effects. In addition, when the cosmetic composition is used as a hair dye composition, it can impart the above-mentioned effects to hair and secure good color consistency with little fading by shampooing.

The reason why the cosmetic composition of the present invention exhibits the above-mentioned effect is, though not clear, presumed as follows.

The cosmetic composition containing the component (A) and the component (B) is, when applied to the surface of a keratin substance, able to form a hydrophobic film.

The component (B) has polyalkylene oxide moiety and a cationic group and is therefore considered to have high adsorbability to a keratin substance such as skin or hair to be eccentrically located on the side of the keratin substance to thereby firmly adsorb the formed film to the surface of the keratin substance to exhibit the film peeling preventing effect.

On the other hand, the component (A) is a hydrophobic film forming agent and, is considered to maintain the strength and the durability of the entire film formed and, when combined with the component (B), to be excellent in the adhesiveness to a keratin substance and in the followability to the shape change and the movement of a keratin substance to thereby exhibit an effect of imparting a smooth feel. In addition, in the case where a functional powder to be mentioned below is incorporated in the cosmetic composition, it is considered that the component (A) can keep the functional powder in the film to thereby enhance various functions and the sustainability thereof of the powder.

Further, the water content in the cosmetic composition is 50% by mass or less, and therefore no precipitate may form with time, and the drying speed is high, and even in leave-on use without rinsing away with water, the composition can still impart a smooth feel.

Consequently, for example, in the case where the cosmetic composition is a hair cosmetic composition, and even when applied to hair in a dry state like an leave-on treatment agent and left as such without rinsing away with water, the composition is considered to be still able to impart a smooth feel to the hair in a dry state and in rinsing, and in addition, even after rinsing, these effects can sustain well. Also in the case where the cosmetic composition is a hair dye composition such as a temporary hair dye composition or a semipermanent hair dye composition, it is considered that the composition can impart the above-mentioned effect to hair owing to the synergistic effect of the component (A) and the component (B), and can improve color consistency with little fading by shampooing.

The mechanism of the action of the present invention is not limited to the above.

Components contained in the cosmetic composition of the present invention are described below.

<Component (A): Silicone Film-forming Agent>

The cosmetic composition of the present invention contains a silicone film-forming agent as the component (A). Containing the component (A), the cosmetic composition of the present invention is, when applied to a keratin substance such as skin or hair, able to impart a smooth feel and able to form a highly-durable hydrophobic film when applied to a keratin substance such as skin or hair like an leave-on treatment agent. In the case where a functional powder to be mentioned hereinunder is incorporated in the cosmetic composition, the functional powder can be held in the film to improve various functions and sustainability thereof.

As the component (A), a silicone film-forming agent usable in ordinary cosmetic materials can be used, and is preferably solid at 25° C.

From the viewpoint of imparting a smooth feel to a keratin substance such as skin or hair when applied thereto like an leave-on treatment agent, and from the viewpoint of improving film formability and durability, the component (A) is preferably at least one selected from the group consisting of the following components (A1) and (A2).

(A1) A silicone resin represented by an average formula,
$(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains at least one unit selected from the group consisting of a T unit represented by $R^1 SiO_{3/2}$ and a Q unit represented by $SiO_{4/2}$.

(A2) A silicone polymer containing a polysiloxane moiety and a moiety formed of a non-silicone organic chain.

Preferably, the component (A1) includes those containing at least one selected from the group consisting of the following component (A1-1) and component (A1-2).

(A1-1) A silicone resin represented by the above-mentioned average formula, containing a T unit represented by $R^1 SiO_{3/2}$ and substantially not containing a Q unit represented by $SiO_{4/2}$.

(A1-2) A silicone resin represented by the above-mentioned average formula, and containing a Q unit represented by $SiO_{4/2}$ and an M unit represented by $(R^1)_3 SiO_{1/2}$.

Preferably, the component (A2) includes those containing at least one selected from the group consisting of the following component (A2-1) to (A2-4).

(A2-1) An acryl silicone polymer.
(A2-2) A silicone-modified alicyclic structure-containing polymer.
(A2-3) A silicone-modified pullulan.
(A2-4) A polyurea/urethane silicone.

Component (A1)

The component (A1) is a silicone resin represented by an average formula, $(R^1)_m S_{(4-m)/2}$ 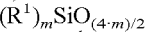
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains at least one unit selected from the group consisting of a T unit represented by $R^1 SiO_{3/2}$ and a Q unit represented by $SiO_{4/2}$.

The component (A1) is represented by the above-mentioned average formula and contains at least one unit selected from the above-mentioned T unit and Q unit, and therefore has a crosslinked structure in the molecule. Having the structure, the silicone resin is considered to be able to form a film having higher durability. The component (A1) does not contain a polyorganosiloxane cured product powder which is infusible and does not have a softening point and which is generally insoluble in an organic solvent.

In the average formula, $R^1$ represents a hydrocarbon group having 1 or more and 12 or less carbon atoms and optionally substituted with fluorine, or a hydroxy group. The carbon number of the hydrocarbon group is, from the viewpoint of improving film formability and durability, 1 or more and preferably 9 or less, more preferably 6 or less, even more preferably 4 or less.

The hydrocarbon group may be any of an aliphatic group or an aromatic group, and examples thereof include an alkyl group, an alkenyl group, an aryl group and an aralkyl group. The alkyl group and the alkenyl group may be linear or branched.

Among the above, from the viewpoint of availability and stability, the hydrocarbon group is preferably an alkyl group, an aryl group or an aralkyl group.

The alkyl group includes a methyl group, an ethyl group, an n-propyl group, an isopropyl group, various butyl groups, various pentyl groups, various hexyl groups, various heptyl groups, various octyl groups, various nonyl group, various decyl groups, various undecyl groups, and various dodecyl groups. The word "various" means a linear or branched hydrocarbon group, and for example, "various butyl groups" include "an n-butyl group, a sec-butyl group, an isobutyl group and a tert-butyl group".

The aryl group includes a phenyl group, a toluyl group, a dimethylphenyl group, and a naphthyl group, and is preferably a phenyl group.

The aralkyl group includes a benzyl group, a phenylethyl group, a phenylpropyl group, and a phenylbutyl group, and is preferably a phenylpropyl group.

In the case where $R^1$ is substituted with fluorine, at least one hydrogen atom of the hydrocarbon group may be substituted with a fluorine atom.

$R^1$ is, from the viewpoint of improving film formability and durability, preferably an optionally fluorine-substituted, alkyl group having 1 or more and 12 or less carbon atoms, aryl group having 6 or more and 12 or less carbon atoms or aralkyl group having 7 or more and 12 or less carbon atoms, more preferably an optionally fluorine-substituted, alkyl group having 1 or more and 8 or less carbon atoms or phenyl group, even more preferably an optionally fluorine-substituted, alkyl group having 1 or more and 6 or less carbon atoms or phenyl group. The fluorine-substituted alkyl group is preferably a group represented by $CF_3$—R— wherein R represents an alkylene group having 2 or more and 7 or less carbon atoms, preferably 2 or more and 5 or less carbon atoms.

$R^1$ is more preferably a trifluoropropyl group, an alkyl group having 1 or more and 4 or less carbon atoms, or a phenyl group, even more preferably a trifluoropropyl group, a methyl group, an ethyl group, an n-propyl group, an isopropyl group or an n-butyl group, further more preferably a trifluoropropyl group, a methyl group or an n-propyl group, and further more preferably a methyl group.

The component (A1) may contain at least one unit selected from the group consisting of a T unit represented by $R^1SiO_{3/2}$ and a Q unit represented by $SiO_{4/2}$ and, from the viewpoint of improving film formability and durability, preferably further contains at least one unit selected from the group consisting of an M unit represented by $(R^1)_3SiO_{1/2}$ and a D unit represented by $(R^1)_2SiO_{2/2}$. $R^1$ is the same as above.

From the viewpoint of imparting a smooth feel to a keratin substance such as skin or hair when applied thereto like an leave-on treatment agent, and from the viewpoint of improving film formability and durability, the component (A1) is preferably at least one selected from the group consisting of a silicone resin (A1-1) represented by the above-mentioned compositional formula, containing a T unit represented by $R^1SiO_{3/2}$ and substantially not containing a Q unit represented by $SiO_{4/2}$, and a silicone resin (A1-2) represented by the above-mentioned compositional formula, and containing a Q unit represented by $SiO_{4/2}$ and an M unit represented by $(R^1)_3SiO_{1/2}$.

[Silicone Resin (A1-1)]

The silicone resin (A1-1) represented by the above-mentioned average formula, containing a T unit represented by $R^1SiO_{3/2}$ and substantially not containing a Q unit represented by $SiO_{4/2}$ (hereinafter also referred to as "component (A1-1)") is a silicone resin containing a T unit and optionally containing an M unit and a D unit, and is preferably a silicone resin containing a T unit and optionally containing an M unit, which is represented by $[R^1SiO_{3/2}]_a[(R^1)_3SiO_{1/2}]_b$ wherein a and b each are an average repeating unit number, and a>0 and b≥0. The wording "substantially not containing XX" means the constituent ratio of XX in the silicone resin is less than 1 mol %.

$R^1$ is the same as above, and is preferably an alkyl group having 1 or more and 4 or less carbon atoms or a phenyl group, more preferably a methyl group, an ethyl group, an n-propyl group or an isopropyl group, even more preferably a methyl group, an n-propyl group or an isopropyl group.

The component (A1-1) includes polysilsesquioxanes such as polymethylsilsesquioxane, polypropylsilsesquioxane, polyphenylsilsesquioxane, polymethylphenylsilsesquioxane, and fluorine-modified alkyldimethylpolysilsesquioxanes, and among these, one or more can be used. Fluorine-modified alkyldimethylpolysilsesquioxanes include, as INCI nomenclature, trifluoropropyldimethylsiloxy/trimethylsiloxy)silsesquioxane.

Above all, from the viewpoint of imparting a smooth feel to a keratin substance such as skin or hair when applied thereto like an leave-on treatment agent, and from the viewpoint of improving film formability and durability, the component (A1-1) is preferably at least one selected from the group consisting of polymethylsilsesquioxane and polypropylsilsesquioxane.

Commercial products of the component (A1-1) include SilForm Flexible Resin (polymethylsilsesquioxane), SilForm FR-5 (polydimethylsiloxane solution of (trifluoropropyldimethylsiloxy/trimethylsiloxy)silsesquioxane) (all by Momentive Performance Materials Corporation), DOWSIL 680 ID Fluid (isododecane solution of 75 mass % polypropylsilsesquioxane) (by Day Toray Corporation), SR-21 (polyphenylsilsesquioxane), SR-23 (polyphenylsilsesquioxane), SR-33 (polymethylphenylsilsesquioxane) (all by Konishi Chemical Industry Co., Ltd.).

[Silicone Resin (A1-2)]

The silicone resin (A1-2) represented by the above-mentioned average formula, and containing a Q unit represented by $SiO_{4/2}$ and an M unit represented by $(R^1)_3SiO_{1/2}$ (hereinafter also referred to as "component (A1-2)") is a silicone resin substantially containing a Q unit and an M unit and optionally containing a D unit or a T unit, and is preferably a silicone resin represented by $[SiO_{4/2}]_c[(R^1)_3SiO_{1/2}]_d$ wherein c and d each are an average repeating unit number and c>0 and d>0.

$R^1$ is the same as above, and is preferably an optionally-fluorine substituted, alkyl group having 1 or more and 6 or less carbon atoms or phenyl group, more preferably a trifluoropropyl group, an alkyl group having 1 or more and 4 or less carbon atoms, or a phenyl group, even more preferably a trifluropropyl group, methyl group, an ethyl group, an n-propyl group, or an isopropyl group, further more preferably a trifluoropropyl group or a methyl group, and further more preferably a methyl group.

The component (A1-2) includes trimethylsiloxysilicate, phenylpropyldimethylsiloxysilicate, fluorine-modified alkyldimethylsiloxysilicates, and crosspolymers produced by crosslinking these siloxysilicates with dimethiconol, and at least one of these can be used. Fluorine-modified alkyldimethylsiloxysilicates include trifluoroalkyldimethyltrimethylsiloxysilicate, such as trifluoropropyldimethyltrimethylsiloxysilicate of, as ICNI nomenclature, trifluoropropyldimethyl/trimethylsiloxysilicate. Crosspolymers produced by crosslinking siloxysilicates with dimethiconol include, as ICNI nomenclature, (trimethylsiloxysilicate/dimethiconol) crosspolymer.

Above all, from the viewpoint of imparting a smooth feel to a keratin substance such as skin or hair when applied thereto like an leave-on treatment agent, and from the viewpoint of improving film formability and durability, the component (A1-2) is preferably at least one selected from the group consisting of trimethylsiloxysilicate, trifluoropropyldimethyltrimethylsiloxysilicate and (trimethylsiloxysilicate/dimethiconol) crosspolymer, more preferably at least one selected from the group consisting of trimethylsiloxysilicate, and trifluoropropyldimethyltrimethylsiloxysilicate, even more preferably trimethylsiloxysilicate.

Commercial products of trimethylsiloxysilicate of the component (A1-2) include KF-7312J (50 mass % decamethylcyclopentasiloxane solution), KF-9021 (50 mass % decamethylcyclopentasiloxane solution), X-21-5249 (50 mass % decamethylcyclopentasiloxane solution), X-21-5595 (60 mass % isododecane solution), and X-21-5616 (60 mass % isododecane solution) (all by Shin-Etsu Chemical Industry Co., Ltd.), SS4267 (35 mass % dimethylpolysiloxane solution), SR1000, SS4230 (45 mass % cyclopentasiloxane solution), SS4267 (35 mass % dimethylpolysiloxane solution), and Silsoft 74 (75 mass % isododecane solution) (all by Momentive Performance Materials Corporation), BY11-018 (30 mass % cyclopentasiloxane solution), and MQ-1600 Solid Resin (all by Dow Toray Corporation), and BELSIL TMS 803 (by Wacker Asahi Kasei Silicone Co., Ltd.).

Commercial products of phenylpropyldimethylsiloxysilicate include SilShine 151 (by Momentive Performance Materials Corporation).

Commercial products of fluorine-modified alkyldimethylsiloxysilicates include, XS66-B8226 (50 mass % cyclopentasiloxane solution), XS66-C1191, and XS66-B8636 (50 mass % dimethicone solution) (all by Momentive Performance Materials Corporation), as INCI nomenclature, (trifluoropropyldimethyl/trimethylsiloxysilicate).

Commercial products of trimethylsiloxysilicate crosspolymer include DOWSIL FC-5002 IDD Resin Gum (40 mass % isododecane solution of (trimethylsiloxysilicate/dimethicol) crosspolymer) (by Dow Toray Corporation).

(Component (A2))

The component (A2) is a silicone polymer containing a polysiloxane moiety and a moiety formed of a non-silicone organic chain. The non-silicone organic monomer to constitute the moiety of a non-silicone organic chain is, from the viewpoint of availability on the market, preferably selectable from a radical-polymerizable ethylenically-unsaturated monomer, a polycondensation-polymerizable monomer (e.g., those to form polyamides, polyesters or polyurethanes), and a ring-cleavable monomer (e.g., oxazoline or caprolactone-type ones).

Preferably, the component (A2) includes those containing at least one selected from the group consisting of the following component (A2-1) to (A2-4), more preferably those containing the component (A2-1).

(A2-1) An acryl silicone polymer.
(A2-2) A silicone-modified alicyclic structure-containing polymer.
(A2-3) A silicone-modified pullulan.
(A2-4) A polyurea/urethane silicone.

[Acryl Silicone Polymer (A2-1)]

The acryl silicone polymer of the component (A2-1) includes an acrylic polymer having a carbosiloxane dendrimer structure in the side chain, an acryl-silicone graft copolymer, and a graft-type copolymer or alternate block-type copolymer where a structural unit of a polysiloxane group and a structural unit of a polymer of an unsaturated monomer bond via a sulfide bond.

The acrylic polymer having a carbosiloxane dendrimer structure in the side chain includes a silicone dendrimer-acryl copolymer, and for example, can be produced according to the production method described in JP H11-1530 A and JP 2000-63225 A.

The acrylic polymer having a carbosiloxane dendrimer structure in the side chain is preferably, as INCI nomenclature, acrylates/polytrimethylsiloxymethacrylate copolymer. Commercial products thereof include DOWSIL FA 4001 CM Silicone Acrylate (30 mass % decamethylcyclopentasiloxane solution), DOWSIL FA 4002 ID Silicone Acrylate (40 mass % isododecane solution) (all by Dow Toray Corporation).

The acryl-silicone graft copolymer includes a radical polymer of an organopolysiloxane compound having a radical polymerizable group at one terminal of the molecular chain and a radical polymerizable monomer mainly composed of an acrylate and/or a methacrylate.

Examples of the radical polymer of an organopolysiloxane compound having a radical polymerizable group at one terminal of the molecular chain and a radical polymerizable monomer mainly composed of an acrylate and/or a methacrylate usable here include those described in JP H2-25411 A and JP H2-132141 A, and acryl-silicone graft copolymers described in JP H3-162442 A and JP 2003-104825 A.

The acryl-silicone graft copolymer is preferably, as INCI nomenclature, (acrylates/dimethicone) copolymer. Commercial products thereof include KP-545 (30 mass % decamethylcyclopentasiloxane solution), KP-549 (40 mass % methyltrimethicone solution), and KP-550 (40 mass % isododecane solution) (all by Shin-Etsu Chemical Industry Co., Ltd.).

The graft-type copolymer or alternate block-type copolymer where a structural unit of a polysiloxane group and a structural unit of a polymer of an unsaturated monomer bond via a sulfide bond include graft-type copolymers or alternate block-type copolymers described in JP H6-92825 A.

Above all, from the viewpoint of improving the feel in use and shampooing durability, the component (A2-1) is preferably at least one selected from the group consisting of an acrylic polymer having a carbosiloxane dendrimer structure in the side chain and an acryl-silicone graft copolymer, more preferably at least one selected from (acrylates/polytrimethylsiloxymethacrylate) copolymer and (acrylates/dimethicone) copolymer.

[Silicone-Modified Alicyclic Structure-Containing Polymer (A2-2)]

Examples of the silicone-modified alicyclic structure-containing polymer include silicone-modified cyclic polyolefins, and preferred examples thereof include silicone-modified polynorbornenes represented by the following general formula (A2-2-1).

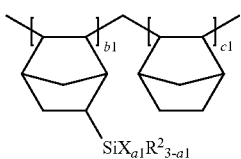
(A2-2-1)

wherein $R^2$ each independently represents an alkyl group having 1 or more and 12 or less carbon atoms, X represents a group represented by the following formula (i), a1 is an integer of 1 or more and 3 or less, b1 and c1 each are a repeating unit number, and are each independently an integer of 1 or more.

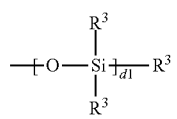
(i)

wherein $R^3$ each independently represents a hydrocarbon group having 1 or more and 12 or less carbon atoms, and d1 is an integer of 1 or more and 5 or less.

In the general formula (A2-2-1), $R^2$ is preferably a methyl group, an ethyl group, an n-propyl group, a butyl group or a pentyl group, more preferably a methyl group.

X is a group represented by the formula (i), and in the formula (i), $R^3$ each are independently a hydrocarbon group having 1 or more and 12 or less carbon atoms. $R^3$ is preferably an alkyl group having 1 or more and 12 or less or a phenyl group, more preferably an alkyl group having 1 or more and 3 or less carbon atoms, even more preferably a methyl group. d1 is an integer of 1 or more and 5 or less, and is, from the viewpoint of versatility, preferably d1=1. Specifically, X is preferably a trimethylsiloxy group.

a1 is an integer of 1 or more and 3 or less, and, for example, in the polymer, a repeating unit of a1=2 and a repeating unit of a1=3 may exist as mixed. From the viewpoint of versatility, a1 is preferably 3.

The proportion of b1 and c1 in the general formula (A2-2-1) is preferably b1/c1=20/80 to 90/10 (mol/mol), more preferably 30/70 to 80/20 (mol/mol), even more preferably 50/50 to 70/30 (mol/mol). The proportion of b1 and c1 can be determined by $^1$H-NMR measurement.

The silicone-modified polynorbornene is preferably a silicone-modified polynorbornene represented by the following formula (A2-2-2).

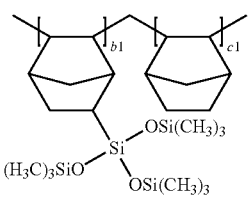
(A2-2-2)

wherein b1 and c1 are the same as above.

The silicone-modified polynorbornene represented by the general formula (A2-2-2) include a compound of, as INCI nomenclature, (norbornene/tris(trimethylsiloxy)silylnorbornene copolymer).

Commercial products of the silicone-modified polynorbornene include NBN-30-ID (isododecane solution of (norbornene/tris(trimethylsiloxy)silylnorbornene) copolymer) (by Shin-Etsu Chemical Industry Co., Ltd.).

[Silicone-Modified Pullulan (A2-3)]

The silicone-modified pullulan includes a pullulan having a silicone structure in the side chain, and specifically preferred is a silicone-modified pullulan in which at least a part of the hydrogen atoms of the OH groups in pullulan are substituted with a group represented by the following general formula (ii).

(ii)

wherein $R^4$ represents a single bond or a divalent organic group, and $R^2$, X and a1 are the same as above. From the viewpoint of versatility, X is preferably a trimethylsiloxyl group, and a1 is preferably 3.

In the general formula (ii), $R^4$ is preferably a divalent organic group, more preferably a divalent group represented by the following general formula (iii) or (iv), even more preferably a divalent group represented by the general formula (iv).

(iii)

(iv)

wherein $R^5$ represents an alkylene group having 1 or more and 10 or less carbon atoms, and examples thereof include a methylene group, an ethylene group, a trimethylene group, a propylene group and a butylene group. Among these, preferred are an ethylene group, a trimethylene group and a propylene group; and more preferred are a trimethylene group and a propylene group.

Commercial products of the silicone-modified pullulan include TSPL-30-ID (isododecane solution of tri(trimethylsiloxy)silylpropylcarbamate pullulan), and TSPL-30-D5 (cyclopentasiloxane solution of tri(trimethylsiloxy)silylpropylcarbamate pullulan) (all by Shin-Etsu Chemical Industry Co., Ltd.).

[Polyurea/Urethane Silicone (A2-4)]

The polyurea/urethane silicone of the component (A2-4) includes a polysiloxane/polyurea/polyurethane block terpolymer. For example, it is a dimethylpolysiloxane/urea copolymer of "polyurea-dimethicone" as INCI nomenclature.

The polymer can be produced by copolymerization of an α, ω-aminosilicone and a diisocyanate. Commercial products of the polyurea/urethane silicone include Wacker-Belsil UD 60, Wacker-Belsil UD 80, Wacker-Belsil UD 140 and Wacker-Belsil UD 200 (all by Wacker Corporation).

One or more can be used as the component (A). Among the above, from the viewpoint of imparting a smooth feel to a keratin substance such as skin or hair when applied thereto like an leave-on treatment agent, and from the viewpoint of improving film formability and durability, the component (A) preferably contains at least one selected from the group consisting of the component (A1), the component (A2-1) and the component (A2-2), more preferably at least one selected from the group consisting of the component (A1)

and the component (A2-1), and even more preferably contains the component (A1), further more preferably the component (A1-2).

More specifically, from the viewpoint of imparting a smooth feel to a keratin substance such as skin or hair when applied thereto like an leave-on treatment agent, and from the viewpoint of improving film formability and durability, the component (A) preferably contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, polypropylsilsesquioxane, (acrylates/polytrimethylsiloxymethacrylate) copolymer, (acrylates/dimethicone) copolymer, and (norbornene/tris(trimethylsiloxy)silylnorbornene) copolymer, more preferably contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, polypropylsilsesquioxane, (acrylates/polytrimethylsiloxymethacrylate) copolymer, and (acrylates/dimethicone) copolymer, even more preferably contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, and polypropylsilsesquioxane, further more preferably contains at least one selected from the group consisting of trimethylsiloxysilicate, trifluoropropyldimethyltrimethylsiloxysilicate, and (trimethylsiloxysilicate/dimethiconol) crosspolymer, further more preferably contains at least one selected from the group consisting of trimethylsiloxysilicate, and trifluoropropyldimethyltrimethylsiloxysilicate, further more preferably contains trimethylsiloxysilicate, and is further more preferably trimethylsiloxysilicate.

<Component (B): Organopolysiloxane Having Polyalkylene Oxide Moiety and Cationic Group Other Than Component (A)>

The cosmetic composition of the present invention contains, as a component (B), an organopolysiloxane having a polyalkylene oxide moiety and a cationic group other than the component (A). The component (B) has high adsorbability to a keratin substance such as skin or hair, and is considered to firmly adsorb the formed film to the surface of the substance to impart wash resistance.

The cationic group that the component (B) has includes a cation group or a group capable of being ionized to be a cation group. Specifically, the group includes a primary amino group, a secondary amino group, a tertiary amino group, and a quaternary ammonium group, and is, from the viewpoint of adsorbability to the surface of skin or hair, preferably at least one selected from the group consisting of a primary amino group, a secondary amino group and a tertiary amino group.

The carbon number of the alkylene oxide to constitute the polyalkylene oxide moiety of the component (B) may be 1 or more, and is, from the viewpoint of availability, preferably 2 or more, preferably 6 or less, more preferably 4 or less, even more preferably 3 or less. A specific range of the carbon number of the alkylene oxide to constitute the polyalkylene oxide moiety of the component (B) is preferably 1 to 6, more preferably 2 to 6, even more preferably 2 to 4, further more preferably 2 to 3, further more preferably 2.

One or more kinds of alkylene oxides may constitute the polyalkylene oxide moiety.

Specific examples of the alkylene oxide include at least one selected from the group consisting of ethylene oxide, propylene oxide, trimethylene oxide, butylene oxide, tetramethylene oxide, pentamethylene oxide, and hexamethylene oxide. Among these, from the viewpoint of availability, the alkylene oxide to constitute the polyalkylene oxide moiety is preferably at least one selected from the group consisting of ethylene oxide, propylene oxide, trimethylene oxide, butylene oxide and tetramethylene oxide, more preferably at least one selected from the group consisting of ethylene oxide, propylene oxide and trimethylene oxide, even more preferably at least one selected from the group consisting of ethylene oxide and propylene oxide, and is, from the viewpoint of making the component (B) eccentrically localized on the keratin substance side in the formed film, further more preferably ethylene oxide.

The average addition molar number of the alkylene oxide in the polyalkylene oxide moiety of the component (B) is, though not specifically limited thereto, preferably 2 or more, more preferably 4 or more, even more preferably 10 or more. From the viewpoint of availability, it is preferably 100 or less, more preferably 80 or less, further more preferably 50 or less. A specific range of the average addition molar number of the alkylene oxide in the polyalkylene oxide moiety of the component (B) is preferably 2 to 100, more preferably 4 to 100, even more preferably 4 to 80, further more preferably 4 to 50, further more preferably 10 to 50.

In the component (B), the polyalkylene oxide moiety and the cationic group may be in the organosiloxane main chain, or may be in the side chain part.

More specifically, the component (B) is more preferably at least one selected from the group consisting of an aminopolyether-modified silicone (B1) having a repeating unit represented by the following general formula (1) and an aminopolyether-modified silicone (B2) having a repeating unit represented by the following general formula (2).

In the following description, the aminopolyether-modified silicone (B1) having a repeating unit represented by the following general formula (1) may also be referred to as "component (B1)", and the aminopolyether-modified silicone (B2) having a repeating unit represented by the following general formula (2) may be as "component (B2)".

(Component (B1))

The component (B1) is an aminopolyether-modified silicone having a repeating unit represented by the following general formula (1).

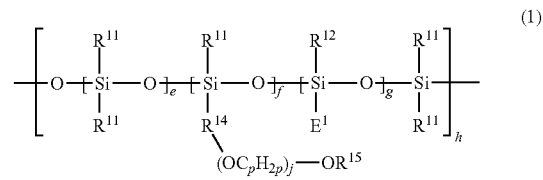

In the formula (1), $R^{11}$ represents a monovalent hydrocarbon group having 1 or more and 6 or less carbon atoms, $R^{12}$ represents any of $R^{11}$ or $E^1$, $E^1$ represents a monovalent group represented by $-R^{13}-Z^1$ (where $R^{13}$ represents a divalent hydrocarbon group having 1 or more and 6 or less carbon atoms, $Z^1$ represents a primary to tertiary amino group-containing group), $R^{14}$ represents a divalent hydrocarbon group having 1 or more and 6 or less carbon atoms, $R^{15}$ represents a hydrogen atom or a monovalent hydrocarbon group having 1 or more and 4 or less carbon atoms.

e is a number of 1 or more and 50 or less, f is a number of 1 or more and 50 or less, g is a number of 1 or more and 50 or less, h is a number of 1 or more, j is a number of 2 or more and 100 or less, p is a number of 2 or more and 10 or less. The bonding order of the parenthesized structural units is not limited, and the bonding form thereof may be in a block form or a random form. j's ($OC_pH_{2p}$)s can be the same or different. Plural $R^{11}$'s, $R^{12}$'s, $R^{14}$'s, $R^{15}$'s and $E^1$'s can be the same or different.

In the general formula (1), $R^{11}$ represents a monovalent hydrocarbon group having 1 or more and 6 or less carbon atoms, and is preferably an alkyl group having 1 or more and 6 or less carbon atoms, or a phenyl group, more preferably a methyl group or an ethyl group, even more preferably a methyl group. $R^{12}$ is any of $R^{11}$ or $E^1$, and is preferably $R^{11}$.

In the general formula (3), $E^1$ represents a monovalent group represented by —$R^{13}$—$Z^1$ (where $R^{13}$ represents a divalent hydrocarbon group having 1 or more and 6 or less carbon atoms, $Z^1$ represents a primary to tertiary amino group-containing group). $R^{13}$ is preferably a divalent hydrocarbon group having 2 or more and 4 or less carbon atoms, more preferably an ethylene group, a trimethylene group, a propylene group or a tetramethylene group.

$Z^1$ is a primary to tertiary amino group-containing group, and is preferably a group represented by —$N(R^{16})_2$, —$NR^{16}(CH_2)_qN(R^{16})_2$, or —$NR^{16}(CH_2)_qN(R^{17})CO$—$R^{18}$. Here, $R^{16}$ represents a hydrogen atom or a monovalent hydrocarbon group having 1 or more and 4 or less carbon atoms, preferably a hydrogen atom, a methyl group or an ethyl group. $R^{17}$ represents a monovalent hydrocarbon group having 1 or more and 4 or less carbon atoms, and is preferably a methyl group or an ethyl group. $R^{18}$ represents a monovalent hydrocarbon group having 1 or more and 4 or less carbon atoms. q is a number of 2 or more and 6 or less, and is preferably a number of 2 or more and 4 or less.

In the general formula (1), the group $E^1$ is preferably —$(CH_2)_3$—$NH_2$, —$(CH_2)_3$—$N(CH_3)_2$, —$(CH_2)_3$—$NH$—$(CH_2)_2$—$NH_2$, or —$(CH_2)_2$—$NH$—$(CH_2)_2$—$N(CH_3)_2$, more preferably —$(CH_2)_3$—$NH_2$, or —$(CH_2)_3$—$NH$—$(CH_2)_2$—$NH_2$.

In the general formula (1), $R^{14}$ is a divalent hydrocarbon group having 1 or more and 6 or less carbon atoms, preferably a divalent hydrocarbon group having 2 or more and 4 or less carbon atoms, more preferably an ethylene group, a trimethylene group, a propylene group or a tetramethylene group.

$R^{15}$ is a hydrogen atom or a monovalent hydrocarbon group having 1 or more and 4 or less carbon atoms, and is preferably a methyl group or an ethyl group.

In the general formula (1), e is a number of 1 or more and 50 or less, f is a number of 1 or more and 50 or less, g is a number of 1 or more and 50 or less, h is a number of 1 or more, j is a number of 2 or more and 100 or less. p is a number of 2 or more and 10 or less, preferably 2 or more and 6 or less, more preferably 2 or more and 4 or less.

In particular, the component (B1) is more preferably one represented by the following general formula (1-1).

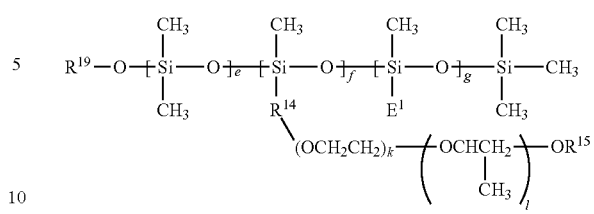

In the formula (1-1), $E^1$, $R^{14}$, $R^{15}$, e, f, and g are the same as above, $R^{19}$ represents a monovalent hydrocarbon group having 1 or more and 4 or less carbon atoms, or a trimethylsilyl group, k is a number of 1 or more and 50 or less, l is a number of 0 or more and 50 or less, and is preferably 1 or more and 50 or less.

$R^{19}$ is preferably a methyl group, an ethyl group or a trimethylsilyl group, more preferably a trimethylsilyl group.

As the component (B1), one or more can be used either singly or as combined.

As the component (B1), commercially-available aminopolyether-modified silicones can be used. Examples thereof include ABIL Soft AF100 (aminopolyether-modified silicone represented by the general formula (1-1) (methoxy PEG/PPG-7/3 aminopropyl dimethicone)) (by Evonik Corporation).

(Component (B2))

The component (B2) is an aminopolyether-modified silicone having a repeating unit represented by the following general formula (2).

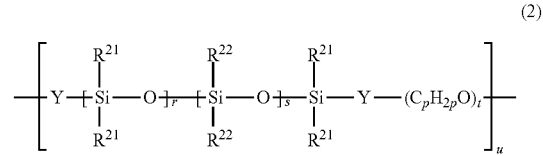

In the formula (2), $R^{21}$ represents a monovalent hydrocarbon group having 1 or more and 6 or less carbon atoms, $R^{22}$ represents any of $R^{21}$ or $E^2$, $E^2$ represents a monovalent group represented by —$R^{23}$—$Z^2$ (where $R^{23}$ represents a single bond, or a divalent hydrocarbon group having 1 or more and 20 or less carbon atoms, $Z^2$ represents a primary to tertiary amino group-containing group), Y represents a single bond, or a divalent group having 1 or more and 12 or less carbon atoms. In the case where all $R^{22}$'s are $R^{21}$'s, at least one Y is an amino group-containing divalent group. In the case where all Y's are divalent groups not containing an amino group, at least one $R^{22}$ is $E^2$.

r is a number of 1 or more, s is a number of 1 or more, t is a number of 2 or more and 100 or less, u is a number of 1 or more. p is the same as above, and is a number of 2 or more and 10 or less. The bonding order of the parenthesized structural units is not limited, and the bonding form thereof may be in a block form or a random form. t's ($C_pH_{2p}O$)s can be the same or different. Plural $R^{21}$'s, $R^{22}$'s, $E^2$'s and Y's can be the same or different.

In the general formula (2), $R^{21}$ represents a monovalent hydrocarbon group having 1 or more and 6 or less carbon atoms, and is independently preferably an alkyl group having 1 or more and 6 or less carbon atoms, or a phenyl group, more preferably a methyl group or an ethyl group, even more preferably a methyl group.

In the general formula (2), $R^{22}$ is any of $R^{21}$ or $E^2$. $E^2$ represents a monovalent group represented by $-R^{23}-Z^2$ (where $R^{23}$ represents a single bond, or a divalent hydrocarbon group having 1 or more and 20 or less carbon atoms).

$R^{23}$ is preferably a divalent hydrocarbon group having 1 or more and 20 or less carbon atoms, more preferably an alkylene group having 1 or more and 20 or less carbon atoms, even more preferably a linear or branched alkylene group having 1 or more and 6 or less carbon atoms, further more preferably a methylene group, an ethylene group, a trimethylene group, a propylene group, a tetramethylene group, or a hexamethylene group, further more preferably a trimethylene group or a propylene group.

$Z^2$ is a primary to tertiary amino group-containing group, and is preferably an amino group-containing group represented by $-N(R^{24})_2$, $-NR^{24}(CH_2)_qN(R^{24})_2$, or $-NR^{24}(CH_2)_qN(R^{25})CO-R^{26}$. Here, $R^{24}$ and $R^{25}$ each independently represent a hydrogen atom or an alkyl group having 1 or more and 3 or less carbon atoms, preferably a hydrogen atom or a methyl group. $R^{26}$ represents an alkyl group having 1 or more and 3 or less carbon atoms, q is a number of 1 or more and 6 or less, and is preferably a number of 2 or more and 4 or less.

In the general formula (2), the group $E^2$ is preferably $-(CH_2)_3-NH_2$, $-(CH_2)_3-N(CH_3)_2$, $-(CH_2)_3-NH-(CH_2)_2-NH_2$, or $-(CH_2)_2-NH-(CH_2)_2-N(CH_3)_2$, more preferably $-(CH_2)_3-NH_2$, or $-(CH_2)_3-NH-(CH_2)_2-NH_2$.

In the general formula (2), Y is a single bond, or a divalent group having 1 or more and 12 or less carbon atoms. The divalent group having 1 or more and 12 or less carbon atoms is preferably an alkylene group having 1 or more and 6 or less carbon atoms, an alkyleneoxy group having 1 or more and 6 or less carbon atoms, or a divalent group represented by $-R^{27}-O-CH_2-CH(OH)-CH_2-N(R^{28})-R^{29}-O-$ of an amino group-containing divalent group. Here, $R^{27}$ and $R^{29}$ each independently represent an alkylene group having 1 or more and 6 or less carbon atoms, preferably an alkylene group having 2 or more and 4 or less carbon atoms, more preferably a propylene group. $R^{28}$ represents a hydrogen atom or an alkyl group having 1 or more and 3 or less carbon atoms.

In the general formula (2), the alkylene group having 1 or more and 6 or less carbon atoms and the alkylene group in the alkyleneoxy group having 1 or more and 6 or less carbon atoms for Y are preferably an ethylene group, a propylene group, a trimethylene group, an n-butylene group (tetramethylene group) or an isobutylene group, more preferably an n-butylene group or an isobutylene group. The isobutylene group as referred to herein includes $-CH(CH_3)CH_2CH_2-$, $-CH_2CH(CH_3)CH_2-$, and $-CH_2CH_2CH(CH_3)-$.

In the general formula (2), r is a number of 1 or more, s is a number of 1 or more, t is a number of 2 or more and 100 or less, u is a number of 1 or more. r is preferably a number of 1 or more and 1000 or less, more preferably a number of 2 or more and 200 or less. s is preferably a number of 1 or more and 100 or less, t is preferably a number of 4 or more and 80 or less, more preferably 10 or more and 50 or less, u is preferably a number of 1 or more and 300 or less, more preferably a number of 1 or more and 150 or less.

In the general formula (2), p is a number of 2 or more and 10 or less, preferably 2 or more and 6 or less, more preferably 2 or more and 4 or less.

The component (B2) is more preferably at least one selected from the group consisting of an aminopolyether-modified silicone having a structure represented by the following general formula (2-1) and an aminopolyether-modified silicone having a structure represented by the following general formula (2-2). Even more preferably, the component is at least one selected from the group consisting of an aminopolyether-modified silicone composed of a structure represented by the following general formula (2-1) and an aminopolyether-modified silicone composed of a structure represented by the following general formula (2-2), further more preferably an aminopolyether-modified silicone composed of a structure represented by the following general formula (2-1).

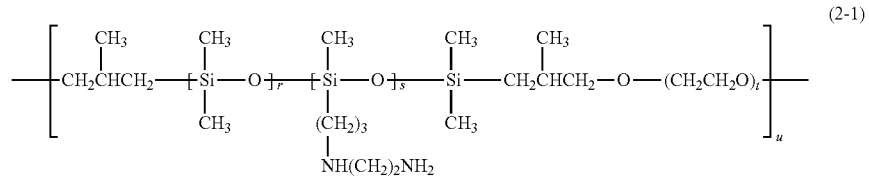

In the formula (2-1), r, s, t and u are the same as above.

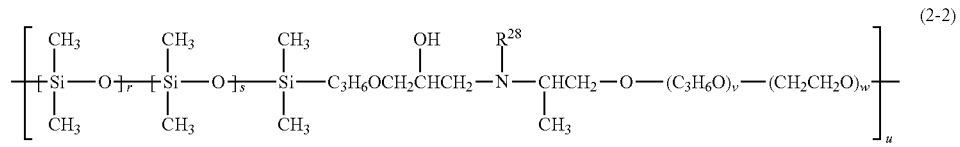

In the formula (2-2), $R^{28}$, r, s and u are the same as above. v is a number of 0 or more and 50 or less, preferably 2 or more and 50 or less. w is a number of 2 or more and 100 or less. v+w is a number of 2 or more and 100 or less, preferably 4 or more and 80 or less, more preferably 10 or more and 50 or less.

As the component (B2), one or more can be used either singly or as combined.

As the component (B2), commercially-available aminopolyether-modified silicones can be used. Examples thereof include, as the aminopolyether-modified silicone having a structure represented by the general formula (2-1), DOWSIL SS-3588 Fluid ((bisisobutyl-PEG-15/amodimethicone) copolymer), DOWSIL SILSTYLE 104 ((bisisobutyl-PEG-14/amodimethicone) copolymer), DOWSIL SILSTYLE 201 ((bisisobutyl-PEG-14/amodimethicone) copolymer), DOWSIL SILSTYLE 401 ((bisisobutyl PEG/PPG-20/35/amodimethicone) copolymer) (all by Dow Toray Corporation), and include, as the aminopolyether-modified silicone having a structure represented by the general formula (2-2), Silsoft A+ (PEG-40/PPG-8 methylaminopropyl/hydroxypropyldimethicone copolymer) (by Momentive Performance Materials Corporation).

As the component (B), one or more of the above can be used either singly or as combined. In particular, from the viewpoint of good adsorbability to the surfaces of keratin substances such as skin or hair, and from the viewpoint of improving wash resistance, the component (B) is preferably an aminopolyether-modified silicone (B2) having a repeating unit represented by the above general formula (2), more preferably an aminopolyether-modified silicone having a structure of the above general formula (2-1), or an aminopolyether-modified silicone having a structure of the above general formula (2-2), even more preferably an aminopolyether-modified silicone having a structure of the above general formula (2-1).

<Content>

The content of the component (A) in the cosmetic composition is, from the viewpoint of imparting a smooth feel to a keratin substance such as skin or hair, when applied thereto like an leave-on treatment agent, and from the viewpoint of improving film formability and durability, preferably 1% by mass or more, more preferably 1.5% by mass or more, even more preferably 2% by mass or more, further more preferably 3% by mass or more, and is, from the viewpoint of improving a smooth feel and from the viewpoint of improving the sustainability of various effects after washing, preferably 50% by mass or less, more preferably 35% by mass or less, even more preferably 20% by mass or less, further more preferably 15% by mass or less. A specific range of the content of the component (A) in the cosmetic composition of the present invention is preferably 1 to 50% by mass, more preferably 1.5 to 35% by mass, even more preferably 1.5 to 20% by mass, further more preferably 2 to 15% by mass, further more preferably 3 to 15% by mass.

The content of the component (B) in the cosmetic composition is, from the viewpoint of improving sustainability of various effects after washing, preferably 0.1% by mass or more, more preferably 0.2% by mass or more, even more preferably 0.5% by mass or more, further more preferably 1% by mass or more, further more preferably 1.3% by mass or more, and is, from the viewpoint of imparting a smooth feel to the surfaces of keratin substances such as skin or hair in use like an leave-on treating agent, preferably 15% by mass or less, more preferably 10% by mass or less, even more preferably 8% by mass or less, further more preferably 5% by mass or less, further more preferably 3% by mass or less. A specific range of the content of the component (B) in the cosmetic composition of the present invention is preferably 0.1 to 15% by mass, more preferably 0.2 to 10% by mass, even more preferably 0.5 to 8% by mass, further more preferably 0.5 to 5% by mass, further more preferably 0.5 to 3% by mass, further more preferably 1 to 3% by mass, further more preferably 1.3 to 3% by mass.

The total content of the component (A) and the component (C) in the cosmetic composition of the present invention is, from the viewpoint of imparting a smooth feel to keratin substances such as skin or hair in leave-on use, and from the viewpoint of improving sustainability of various effects after washing, preferably 1% by mass or more, more preferably 2% by mass or more, even more preferably 3% by mass or more, and is preferably 50% by mass or less, more preferably 25% by mass or less, even more preferably 20% by mass or less, further more preferably 18% by mass or less. A specific range of the total content of the component (A) and (B) in the cosmetic composition of the present invention is preferably 1 to 50% by mass, more preferably 2 to 25% by mass, even more preferably 3 to 20% by mass, further more preferably 3 to 18% by mass.

A ratio of the content by mass of the component (B) to the content by mass of the component (A) in the cosmetic composition of the present invention, [(B)/(A)] is, from the viewpoint of smoothness in rinsing after application to a keratin substance such as skin or hair like an leave-on treatment agent, and from the viewpoint of improving sustainability of various effects after washing, preferably 0.05 or more, more preferably 0.10 or more, even more preferably 0.17 or more, further more preferably 0.20 or more, and is, from the viewpoint of improving sustainability of various effects after washing, preferably 50 or less, more preferably 15 or less, even more preferably 8 or less, further more preferably 3 or less, further more preferably 2 or less, further more preferably 1 or less. A specific range of the ratio of the content by mass of the component (B) to the content by mass of the component (A) in the cosmetic composition of the present invention, [(B)/(A)] is preferably 0.05 to 50, more preferably 0.10 to 15, even more preferably 0.10 to 8, further more preferably 0.17 to 5, further more preferably 0.17 to 3, further more preferably 0.17 to 2, further more preferably 0.20 to 1.

<Component (C): Solvent>

From the viewpoint of dissolving or dispersing the component (A), the component (B) and other components, and from the viewpoint of controlling the viscosity to be easily applicable to keratin substances such as skin or hair, the cosmetic composition of the present invention can further contain a solvent as a component (C).

The solvent is, from the viewpoint of easy handleability, preferably a liquid organic solvent, including an alcohol solvent, an ether solvent, a ketone solvent, an ester solvent, a hydrocarbon solvent and a silicone solvent, and these can be appropriately selected depending on the formulation form. Among these, from the viewpoint of bettering sense of use after drying (from the viewpoint of reducing stickiness), a volatile solvent is preferably contained.

Among volatile solvents, the alcohol solvent includes ethanol, 1-propanol, 2-propanol, 1-butanol, 2-butanol and benzyl alcohol; the ether solvent includes diethyl ether, and tetrahydrofuran; the ketone solvent includes acetone, and methyl ethyl ketone; the ester solvent includes methyl acetate, ethyl acetate, butyl acetate and isobutyl acetate; the hydrocarbon solvent includes light liquid isoparaffin (containing, as a main component, isoparaffin having 8 to 16 carbon atoms), pentane, isopentane, hexane, isohexene, heptane, isoheptane, decane, isodecane, dodecane, isododecane, tridecane, isotridecane, tetradecane, and isotetradecane; the silicone solvent includes a cyclic silicone such as decamethylcyclopentasiloxane, dimethylpolysiloxane having a viscosity of 10 mm$^2$/s or less at 25° C., alkyltrimethicone such as methyltrimethicone, and methylphenylpolysiloxane having a viscosity of 20 mm$^2$/s or less . at 25° C. One or more of these can be used. The viscosity is a value measured at 25° C. according to JIS Z8803:2011 "Liquid Viscosity Measurement Method".

From the solubility of the component (A) and the component (B) therein, the component (C) preferably contains at least one selected from the group consisting of dimethylpolysiloxane having a viscosity of 10 mm$^2$/s or less at 25° C. , methyltrimethicone, methylphenylpolysiloxane having a viscosity of 20 mm$^2$/s or less at 25° C., pentane, isopentane, hexane, isohexene, heptane, isoheptane, decane, isodecane, dodecane, isododecane, tetradecane, isotetradecane, tridecane, isotridecane, and light liquid isoparaffin, more preferably at least one selected from the group consisting of dimethylpolysiloxane having a viscosity of 5 mm$^2$/s or less at 25° C., methyltrimethicone, isodecane, isododecane, isotetradecane and light liquid isoparaffin, even more preferably at least one selected from the group consisting of isodecane, isododecane, isotetradecane and light liquid isoparaffin.

From the viewpoint of maintaining good solubility of the component (A) and the component (B) therein, and from the viewpoint of controlling speed for film formation, the component (C) preferably contains a volatile alcohol solvent and at least one of a volatile hydrocarbon solvent or a volatile silicone solvent, more preferably contains at least one selected from the group consisting of ethanol, 1-propanol, 2-propanol, 1-butanol and 2-butanol, and at least one selected from the group consisting of dimethylpolysiloxane having a viscosity of 10 mm$^2$/s or less at 25° C., methyltrimethicone, methylphenylpolysiloxane having a viscosity of 20 mm$^2$/s or less at 25° C., pentane, isopentane, hexane, isohexene, heptane, isoheptane, decane, isodecane, dodecane, isododecane, tetradecane, isotetradecane, tridecane, isotridecane, and light liquid isoparaffin, even more preferably contains ethanol and at least one selected from the group consisting of dimethylpolysiloxane having a viscosity of 5 mm$^2$/s or less at 25° C., methyltrimethicone, isodecane, isododecane, isotetradecane and light liquid isoparaffin, further more preferably contains ethanol and at least one selected from the group consisting of isodecane, isododecane, isotetradecane and light liquid isoparaffin.

In the case where the cosmetic composition of the present invention contains the component (C), the content thereof is, from the viewpoint of dissolving or dispersing the component (A), the component (B) and other components, preferably 40% by mass or more, more preferably 50% by mass or more, even more preferably 60% by mass or more, and is, from the viewpoint of controlling the viscosity of the cosmetic composition to be easily applicable to keratin substances such as skin or hair, preferably 98.9% by mass or less, more preferably 98% by mass or less. A specific range of the content of the solvent in the cosmetic composition of the present invention is preferably 40 go 98.9% by mass, more preferably 50 to 98.9% by mass, even more preferably 60 to 98% by mass.

<Component (D): Functional Powder>

The cosmetic composition of the present invention can further contain a functional powder as a component (D), depending on the product form thereof.

In the present invention, the functional powder means a powder capable of providing various characteristics such as coloring performance, concealing performance, gloss, UV scattering, and feel controlling. In the case where the cosmetic composition of the present invention is a sunscreen cosmetic material, preferably, a UV scattering agent is incorporated therein as the component (D), from the viewpoint of providing a desired sunscreen effect. In the case where the cosmetic composition of the present invention is a makeup cosmetic composition or a hair dye composition, preferably, a pigment is incorporated therein as the component (D), from the viewpoint of providing a desired color tone.

As the UV scattering agent, preferably usable is at least one metal oxide powder selected from the group consisting of zinc oxide, titanium oxide and cerium oxide. An average particle size of the fine particle metal oxide powder is, from the viewpoint of UV protective effect, preferably 100 to 500 nm, more preferably 12 to 100 nm, even more preferably 15 to 50 nm. The average particle size can be measured according to a laser diffraction/scattering method.

The pigment may be any pigment generally used in makeup cosmetic materials and hair dye compositions, and examples thereof include a white inorganic pigment such as titanium oxide, zinc oxide, cerium oxide and barium sulfate; a colored inorganic pigment such as yellow iron oxide, black iron oxide, red iron oxide, carbon black, chromium oxide, chromium hydroxide, Prussian blue and ultramarine blue; a luster powder such as titanium oxide-coated mica, titanium oxide-coated bismuth oxychloride, iron oxide-coated mica titanium, iron oxide mica, Prussian blue-processed mica titanium, carmine-processed mica titanium, bismuth oxychloride, and fish scale guanine; an organic pigment such as Red No. 201, Red No. 202, Red No. 205, Red No. 226, Red No. 228, Orange No. 203, Orange No. 204, Blue No. 404, and Yellow No. 401; a chelate pigment such as a zirconium, barium or aluminum chelate of Red No. 3, Red No. 104, Red No. 106, Orange No. 205, Yellow No. 4, Yellow No. 5, Green No. 3 or Blue No. 1; and a composite pigment such as fine particle titanium oxide-coated mica titanium, fine particle zinc oxide-coated mica titanium, barium sulfate-coated mica titanium, titanium oxide-containing silicone dioxide and zinc oxide-containing silicon dioxide. One or more of these can be used either singly or as combined. Those prepared by coating the surfaces of these functional powders with various surface treatment agents are also usable. The surface treatment agent is not specifically limited. Various surface treatments can be applied to the powders, and examples thereof include fluorine compound treatment, silicone treatment, silicone resin treatment, pendant treatment, silane coupling agent treatment, titanium coupling agent treatment, oil treatment, metal soap treatment, N-acylated lysine treatment, polyethylene glycol treatment, PVA treatment, polyacrylic acid treatment, hyaluronic acid treatment, alginic acid treatment, inorganic compound treatment, plasma treatment and mechanochemical treatment.

In the case where the cosmetic composition of the present invention contains the component (D), the content thereof is, from the viewpoint of providing desired performance, preferably 0.01% by mass or more in the cosmetic composition, more preferably 0.1% by mass or more, even more preferably 0.2% by mass or more, further more preferably 0.3% by mass or more, and is, from the viewpoint of dispersibility in the cosmetic composition and economic efficiency, and from the viewpoint of maintaining a good feel, preferably 50% by mass or less, more preferably 30% by mass or less. A specific range of the content of the component (D) in the cosmetic composition of the present invention is preferably 0.01 to 50% by mass, more preferably 0.1 to 50% by mass, even more preferably 0.2 to 30% by mass, further more preferably 0.3 to 30% by mass.

The cosmetic composition of the present invention can contain components generally used in cosmetic compositions, for example, an oily agent other than the above-mentioned components, water, an antioxidant, a fragrance, a colorant, a dye, a preservative, a thickener, a pH regulator, a blood circulation promoter, a cooling sensation agent, an antiperspirant, a bactericide, a skin activator, a moisturizer and a refrigerant, in addition to the above-mentioned components.

The cosmetic composition of the present invention can be produced according to an ordinary method.

From the viewpoint of improving solubility of the component (A) and the component (B), film formability and temporal stability, the water content in the cosmetic composition of the present invention is 50% by mass or less, preferably 20% by mass or less, more preferably 10% by mass or less, even more preferably less than 5% by mass, further more preferably less than 2% by mass.

From the viewpoint of imparting a smooth feel in application to a keratin substance such as skin or hair like an leave-on treatment agent, and from the viewpoint of improving sustainability of various effects after washing, the content of a solid oil in the cosmetic composition of the present invention is preferably small. The solid oil is an oil that is solid at 25° C., and includes a paraffin wax such as solid paraffin, a polyolefin wax such as polyethylene wax, and beeswax. The content is preferably less than 50% by mass in the cosmetic composition, more preferably less than 20% by mass, even more preferably less than 10% by mass, further more preferably less than 5% by mass, further more preferably less than 1% by mass.

In the cosmetic composition of the present invention, the content of a nonvolatile liquid oily agent except the component (B) is preferably smaller, from the viewpoint of imparting a smooth feel in application to a keratin substance such as skin or hair like an leave-on treatment agent, and from the viewpoint of improving sustainability of various effects after washing. The nonvolatile liquid oily agent is an oily agent that has a boiling point of higher than 260° C. under normal pressure and is liquid at 25° C., and examples thereof include a nonvolatile liquid silicone except the component (B); a triglyceride such as glyceryl trioctanoate, avocado oil, olive oil, sesame oil, rice bran oil, safflower oil, soybean oil, corn oil, rapeseed oil, castor oil, cotton seed oil, and mink oil; a fatty acid such as oleic acid and isostearic acid; an ester oil such as isopropyl myristate, butyl myristate, isopropyl palmitate, ethyl oleate, ethyl linoleate, isopropyl linoleate, cetyl caprylate, hexyl laurate, decyl myristate, decyl oleate, oleyl oleate, isostearyl laurate, isotridecyl myristate, isocetyl myristate, isostearyl myristate, octyl dodecyl myristate, octyl palmitate, isocetyl palmitate, isostearyl palmitate, isodecyl oleate, isopropyl isostearate, cetyl 2-ethylhexanoate, stearyl 2-ethylhexanoate, propylene glycol dicaprylate, propylene glycol dioleate, glyceryl tri-2-ethylhexanoate, glyceryl tri(caprate/caprylate), isononyl isononanoate, diisopropyl sebacate, propylene glycol isostearate, 2-ethylhexyl paramethoxycinnamate, 2-ethoxyethyl paramethoxycinnamate, isopropyl paramethoxycinnamate/diisopropylcinnamate mixture, methylbis(trimethylsiloxy)silylisopentyl trimethoxycinnamate, amyl paradimethylaminobenzoate, 2-ethylhexyl paradimethylaminobenzoate, ethylene glycol salicylate, 2-ethylhexyl salicylate, benzyl salicylate, homomenthyl salicylate, octocrylene, and dimethyldiethylbenzal malonate; and a branched or unsaturated higher alcohol such as 2-octyldodecanol, isostearyl alcohol, and oleyl alcohol. The content thereof is, in the cosmetic composition, preferably less than 50% by mass, more preferably less than 40% by mass, even more preferably less than 30% by mass, further more preferably less than 20% by mass, further more preferably less than 10% by mass.

In the cosmetic composition of the present invention, the content of a volatile cyclic silicone such as decamethylcyclopentasiloxane is preferably small, from the viewpoint of the drying speed after application. This is because a volatile cyclic silicone oil takes a longer time for evaporation than a volatile hydrocarbon oil, and therefore tends to take a long time until drying after application to skin or hair. The content of the volatile cyclic silicone in the cosmetic composition is, from the viewpoint of increasing the drying speed after application, preferably less than 5% by mass in the cosmetic composition, more preferably less than 2% by mass, even more preferably less than 1% by mass, further more preferably less than 0.5% by mass, further more preferably less than 0.1% by mass, and is even further more preferably 0% by mass.

From the viewpoint of imparting a smooth feel to keratin substances such as skin or hair in leave-on use, and from the viewpoint of improving sustainability of various effects after washing, the content of a polyalcohol in the cosmetic composition of the present invention is preferably small. The polyalcohol includes a polyalcohol having a boiling point of higher than 260° C. under normal pressure, and examples thereof include propylene glycol and glycerin. The content is preferably less than 5% by mass in the cosmetic composition, more preferably less than 2% by mass, even more preferably less than 1% by mass, further more preferably less than 0.5% by mass, further more preferably less than 0.1% by mass.

<Formulation Form, etc.>

The formulation form of the cosmetic composition of the present invention is not specifically limited, and depending on the product form thereof, the cosmetic composition can have various formation forms such as liquid, paste, cream, gel, foam, spray and wax. The cosmetic composition of the present invention is preferably a waterless composition. Here, the waterless composition means a composition having a water content of less than 1% by mass, preferably less than 0.5% by mass, more preferably less than 0.1% by mass.

The cosmetic composition of the present invention includes various skin cosmetic compositions, eyebrow or eyelash makeup compositions and hair cosmetic compositions.

The skin cosmetic composition includes various skin cosmetic compositions for makeup, foundation, skincare, sunscreen, etc.

The eyebrow or eyelash makeup composition includes various eyebrow or eyelash makeup compositions such as mascara, mascara base coat, mascara topcoat, and eyebrow mascara.

The hair cosmetic composition includes a hair wash composition such as shampoo, as well as a rinse composition, a conditioner composition, a treatment composition (including non-washing type), a styling composition, a hair dye composition, and a hair tonic composition. Among these, from the viewpoint of the effectiveness of the advantageous effects of the present invention, preferred are a conditioner composition, a treatment composition, a styling composition and a hair dye composition.

The above-mentioned cosmetic composition is preferably a so-called leave-on preparation that is used without washing after application to keratin substances such as skin, eyebrow, eyelash or hair.

[Cosmetic Kit]

The present invention provides a cosmetic kit provided with the following compositions (I) and (II):

(I) a composition containing (A) a silicone film-forming agent, (II) a composition containing (B) an organopolysiloxane having a polyalkylene oxide moiety and a cationic group other than the component (A).

Preferably, the total content of water in the compositions (I) and (II) is 50% by mass or less. The cosmetic kit of the present invention may be further provided with a composition containing neither the component (A) nor the component (B).

The cosmetic kit of the present invention is provided with the above compositions (I) and (II), and before use, the two compositions are mixed and applied to a keratin substance such as skin or hair by coating with the resultant mixture.

Regarding the component (A), the component (B) and preferred embodiments thereof, reference can be made to those described hereinabove for the cosmetic composition.

The constituent compositions to constitute the cosmetic kit can optionally contain, as needed, the solvent (C), the functional powder (D) and other optional components exemplified hereinabove for the cosmetic composition.

Not specifically limited, the concentration of each composition to constitute the cosmetic kit, and the total content of water in the compositions (I) and (II) is 50% by mass or less. Namely, it is preferable that the water content in the cosmetic composition to be obtained by mixing all the compositions constituting the cosmetic kit falls within the above-mentioned range. The water content in the cosmetic composition is preferably 20% by mass or less, more preferably 10% by mass or less, even more preferably less than 5% by mass, further more preferably less than 2% by mass, further more preferably less than 1% by mass, further more preferably less than 0.5% by mass, further more preferably less than 0.1% by mass.

[Treatment Method for Keratin Substances]

From the viewpoint that the cosmetic composition of the present invention can promptly form a film excellent in wash resistance on the surfaces of keratin substances, the present invention also provides a treatment method for keratin substances, including a step of applying the cosmetic composition to a keratin substance and then drying it.

The keratin substance includes skin, eyebrow, eyelash, hair and nails, and is preferably skin, eyelash, eyebrow or hair, more preferably hair. The keratin substance to which the cosmetic composition is applied may be in any of a dry state or wet state, but from the viewpoint of attaining the effects of the present invention, the cosmetic composition is preferably applied to a keratin substance in a dry state.

From the viewpoint of uniform application, and from the viewpoint of improving the uniformity of the structure of the film to be formed, it is preferable that the cosmetic composition of the present invention is temporarily compatibilized or dispersed prior to application to keratin substances, and then applied to the surfaces of keratin substances. As the temporarily compatibilizing or dispersing method, arbitrarily employable is any of a thermodynamical method of heating, a physical method of mechanically imparting shear stress, or a chemical method of adding a compatible solvent. From the viewpoint of user-friendliness, preferably, the cosmetic composition is uniformly compatibilized or dispersed by a physical method of stirring or shaking.

In the case where the cosmetic composition of the present invention is a skin cosmetic composition, or an eyebrow or eyelash cosmetic composition, preferably, the composition is applied to skin or the like and then spontaneously dried. From the viewpoint of maintaining various effects of the skin cosmetic composition, or the eyebrow or eyelash cosmetic composition, it is preferable that the composition is not washed off after drying, and is used as a leave-on preparation.

The skin cosmetic composition and the eyebrow or eyelash cosmetic composition is, after applied to skin, preferably dried before being brought into contact with clothes and other articles. The drying time is not specifically limited so far as, after the skin cosmetic composition has been applied, it can substantially form a film on the surface of skin, eyebrow or eyelash, and the time can be appropriately controlled depending on the coating amount and the coating area, and preferably, the formed film is dried for 4 minutes or less, more preferably 2 minutes or less.

In the case where the cosmetic composition of the present invention is a hair cosmetic composition, from the viewpoint of promptly forming a film excellent in wash resistance on the surface of the keratin substance, it is preferable that the application process includes a step of applying the composition to hair and then drying it. From the viewpoint of maintaining various effects of the hair cosmetic composition, it is preferable that the composition is applied to hair in a dry state and then dried, and is used as a leave-on preparation that is not washed off after application. Drying the hair after application of the hair cosmetic composition thereto may be spontaneous drying, or the hair may be dried using a device such as a hair drier hood, a hand hair drier, or a straight iron.

In the case of using the device, preferably, the hair is dried at a temperature of 40 to 220° C. from the viewpoint of suppressing thermal damages of keratin substances. More preferred is drying with a hair drier hood or a hand hair drier, and the drying temperature is preferably 40 to 110° C., more preferably 50 to 90° C.

The drying time is not specifically limited so far as a film is substantially formed on the surface of hair, and can be appropriately controlled depending on the amount and the quality of hair. For example, the time may fall within a range of 10 seconds to 120 minutes.

After drying, the hair may be brushed for scattering the hair.

In the treatment method of the present invention, the amount of the cosmetic composition to be applied to keratin substances is not specifically limited. In the case of a skin cosmetic composition, in general, the amount falls within a range of 0.1 to 1000 mg per $cm^2$ of skin. In the case of an eyebrow or eyelash cosmetic composition or a hair cosmetic composition, in general, the amount falls within a range of 0.005 to 1 g per gram of eyebrow, eyelash or hair.

[Hair Dyeing Method]

From the viewpoint of promptly forming a film excellent in wash resistance on the surfaces of keratin substances, the present invention further provides a hair dyeing method that includes a step of applying the hair dye composition of the present invention to hair and then drying it.

The hair dye composition of the present invention is applied to hair and then dried, and is used without washing. Drying the hair after applying the hair dye composition thereto may be spontaneous drying, or the hair may be dried with a drier or the like.

By the above-mentioned simple operation, the hair dye composition of the present invention can temporarily or semi-permanently dye hair as an leave-on treatment. In addition, the composition can give a smooth feel to hair, and after washing, these effects can be sustained excellently, and the color consistency can be sustained good with little fading by shampooing.

Regarding the above-mentioned embodiments, the present invention discloses the following.

<1>
A cosmetic composition containing:
(A) a silicone film-forming agent, and
(B) an organopolysiloxane having a polyalkylene oxide moiety and a cationic group other than the component (A), wherein:
the content of water is 50% by mass or less.

<2>
A cosmetic composition containing:
(A) a silicone film-forming agent, and
(B) an organopolysiloxane having a polyalkylene oxide moiety and a cationic group other than the component (A), wherein:
the total content of the component (A) and the component (B) in the cosmetic composition is 3% by mass or more and 18% by mass or less,
a ratio by mass of the component (B) to the component (A) in the cosmetic composition [(B)/(A)] is 0.17 or more and 5 or less,
the content of water is 50% by mass or less.

<3>
A cosmetic composition containing:
(A) a silicone film-forming agent, and
(B) an organopolysiloxane having a polyalkylene oxide moiety and a cationic group other than the component (A), wherein:
the total content of the component (A) and the component (B) in the cosmetic composition is 3% by mass or more and 18% by mass or less,
a ratio by mass of the component (B) to the component (A) in the cosmetic composition [(B)/(A)] is 0.17 or more and 2 or less,
the content of water is 50% by mass or less.

<4>
A cosmetic composition containing:
(A) 1 o 50% by mass of a silicone resin represented by an average formula, $(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains a Q unit represented by $SiO_{4/2}$ and an M unit represented by $(R^1)_3SiO_{1/2}$, and
(B) 0.1 to 15% by mass of an organopolysiloxane having a polyalkylene oxide moiety and a cationic group other than the component (A), in which the carbon number of the alkylene oxide constituting the polyalkylene oxide moiety is 1 to 6, the average addition molar number of the alkylene oxide in the polyalkylene oxide moiety is 2 to 100, and the cationic group is at least one selected from the group consisting of a primary amino group, a secondary amino group and a tertiary amino group, wherein:
the total content of the component (A) and the component (B) in the cosmetic composition is 3% by mass or more and 18% by mass or less,
a ratio by mass of the component (B) to the component (A) in the cosmetic composition [(B)/(A)] is 0.17 or more and 5 or less,
the content of water is 50% by mass or less.

<5>
A cosmetic composition containing:
(A) 1 to 50% by mass of a silicone resin represented by an average formula, $(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains a Q unit represented by $SiO_{4/2}$ and an M unit represented by $(R^1)_3SiO_{1/2}$, and
(B) 0.1 to 15% by mass of an organopolysiloxane having a polyalkylene oxide moiety and a cationic group other than the component (A), in which the carbon number of the alkylene oxide constituting the polyalkylene oxide moiety is 1 to 6, the average addition molar number of the alkylene oxide in the polyalkylene oxide moiety is 2 to 100, and the cationic group is at least one selected from the group consisting of a primary amino group, a secondary amino group and a tertiary amino group, wherein:
the total content of the component (A) and the component (B) in the cosmetic composition is 3% by mass or more and 18% by mass or less,
a ratio by mass of the component (B) to the component (A) in the cosmetic composition [(B)/(A)] is 0.17 or more and 5 or less,
the content of water is 50% by mass or less.

<6>
A cosmetic composition containing:
(A) 1 to 50% by mass of a silicone resin represented by $[SiO_{4/2}]_c[(R^1)_3SiO_{1/2}]_d$ wherein c and d each are an average repeating unit number and c>0 and d>0, and
(B) 0.1 to 15% by mass of an aminopolyether-modified silicone having a repeating unit represented by the following general formula (2),

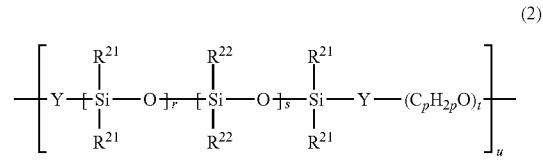

(2)

wherein $R^{21}$ represents a monovalent hydrocarbon group having 1 or more and 6 or less carbon atoms, $R^{22}$ represents any of $R^{21}$ or $E^2$, $E^2$ represents a monovalent group represented by $-R^{23}-Z^2$ (where $R^{23}$ represents a single bond, or a divalent hydrocarbon group having 1 or more and 20 or less carbon atoms, $Z^2$ represents a primary to tertiary amino group-containing group), Y represents a single bond, or a divalent group having 1 or more and 12 or less carbon atoms, in the case where all $R^{22}$'s are $R^{21}$'s, at least one Y is an amino group-containing divalent group, in the case where all Y's are divalent groups not containing an amino group, at least one $R^{22}$ is $E^2$,
r is a number of 1 or more, s is a number of 1 or more, t is a number of 2 or more and 100 or less, u is a number of 1 or more, p is the same as above, and is a number of 2 or more and 10 or less, the bonding order of the parenthesized structural units is not limited, and the bonding form thereof may be in a block form or a random form, t's ($C_pH_{2p}O$)s can be the same or different, plural $R^{21}$'s, $R^{22}$'s, $E^2$'s and Y's can be the same or different, wherein:

the total content of the component (A) and the component (B) in the cosmetic composition is 3% by mass or more and 18% by mass or less, a ratio by mass of the component (B) to the component (A) in the cosmetic composition [(B)/(A)] is 0.17 or more and 5 or less, the content of water is 50% by mass or less.

<7>
A cosmetic composition containing:
(A) 1 to 50% by mass of a silicone resin represented by $[SiO_{4/2}]_c[(R^1)_3SiO_{1/2}]_d$ wherein c and d each are an average repeating unit number and c>0 and d>0, and
(B) 0.1 to 15% by mass of an aminopolyether-modified silicone having a repeating unit represented by the following general formula (2),

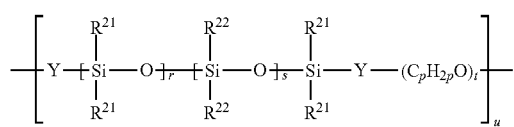

(2)

wherein $R^{21}$ represents a monovalent hydrocarbon group having 1 or more and 6 or less carbon atoms, $R^{22}$ represents any of $R^{21}$ or $E^2$, $E^2$ represents a monovalent group represented by —$R^{23}$—$Z^2$ (where $R^{23}$ represents a single bond, or a divalent hydrocarbon group having 1 or more and 20 or less carbon atoms, $Z^2$ represents a primary to tertiary amino group-containing group), Y represents a single bond, or a divalent group having 1 or more and 12 or less carbon atoms, in the case where all $R^{22}$'s are $R^{21}$'s, at least one Y is an amino group-containing divalent group, in the case where all Y's are divalent groups not containing an amino group, at least one $R^{22}$ is $E^2$, r is a number of 1 or more, s is a number of 1 or more, t is a number of 2 or more and 100 or less, u is a number of 1 or more, p is the same as above, and is a number of 2 or more and 10 or less, the bonding order of the parenthesized structural units is not limited, and the bonding form thereof may be in a block form or a random form, t's ($C_pH_{2p}O$)s can be the same or different, plural $R^{21}$'s, $R^{22}$'s, $E^2$'s and Y's can be the same or different, wherein:

the total content of the component (A) and the component (B) in the cosmetic composition is 3% by mass or more and 18% by mass or less, a ratio by mass of the component (B) to the component (A) in the cosmetic composition [(B)/(A)] is 0.17 or more and 2 or less, the content of water is 50% by mass or less.

<8>
The cosmetic composition according to any one of <1> to <3>, wherein the component (A) is at least one selected from the group consisting of the following components (A1) and (A2), (A1) a silicone resin represented by an average formula, $(R^1)_mSiO_{(4-m)/2}$ wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3, which contains at least one unit selected from the group consisting of a T unit represented by $R^1SiO_{3/2}$ and a Q unit represented by $SiO_{4/2}$, (A2) a silicone polymer containing a polysiloxane moiety and a moiety formed of a non-silicone organic chain.

<9>
The cosmetic composition according to <8>, wherein the component (A1) contains at least one selected from the group consisting of the following component (A1-1) and component (A1-2), (A1-1) a silicone resin represented by the above-mentioned average formula, containing a T unit represented by $R^1SiO_{3/2}$ and substantially not containing a Q unit represented by $SiO_{4/2}$, (A1-2) a silicone resin represented by the above-mentioned average formula, and containing a Q unit represented by $SiO_{4/2}$ and an M unit represented by $(R^1)_3SiO_{1/2}$.

<10>
The cosmetic composition according to <8> or <9>, wherein the component (A2) contains at least one selected from the group consisting of the following components (A2-1) to (A2-4), (A2-1) an acryl silicone polymer,
(A2-2) a silicone-modified alicyclic structure-containing polymer,
(A2-3) a silicone-modified pullulan,
(A2-4) a polyurea/urethane silicone.

<11>
The cosmetic composition according to <9> or <10>, wherein the component (A1) contains the component (A1-2).

<12>
The cosmetic composition according to <10> or <11>, wherein the component (A2) contains the component (A2-1).

<13>
The cosmetic composition according to any one of <1> to <3>, and <8> to <12>, wherein the component (A) contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, polypropylsilsesquioxane, (acrylates/polytrimethylsiloxymethacrylate) copolymer, (acrylates/dimethicone) copolymer, and (norbornene/tris(trimethylsiloxy)silylnorbornene) copolymer, preferably contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, polypropylsilsesquioxane, (acrylates/polytrimethylsiloxymethacrylate) copolymer, and (acrylates/dimethicone) copolymer, more preferably contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, and polypropylsilsesquioxane, even more preferably contains at least one selected from the group consisting of trimethylsiloxysilicate, trifluoropropyldimethyltrimethylsiloxysilicate, and (trimethylsiloxysilicate/dimethiconol) crosspolymer, further more preferably contains at least one selected from the group consisting of trimethylsiloxysilicate, and trifluoropropyldimethyltrimethylsiloxysilicate, further more preferably contains trimethylsiloxysilicate, and is further more preferably trimethylsiloxysilicate.

<14>

The cosmetic composition according to any one of <1> to <5>, and <8> to <13>, wherein the alkylene oxide constituting the polyalkylene oxide moiety of the component (B) is at least one selected from ethylene oxide and propylene oxide.

<15>

The cosmetic composition according to any one of <1> to <3>, and <8> to <14>, wherein the carbon number of the alkylene oxide in the polyalkylene oxide moiety of the component (B) is 1 to 6, the average addition molar number of the alkylene oxide in the polyalkylene oxide moiety is 2 to 100, and the cationic group is at least one selected from the group consisting of a primary amino group, a secondary amino group and a tertiary amino group.

<16>

The cosmetic composition according to any one of <1> to <5>, and <8> to <15>, wherein the component (B) is at least one selected from the group consisting of an aminopolyether-modified silicone (B1) having a repeating unit represented by the following general formula (1) and an aminopolyether-modified silicone (B2) having a repeating unit represented by the following general formula (2),

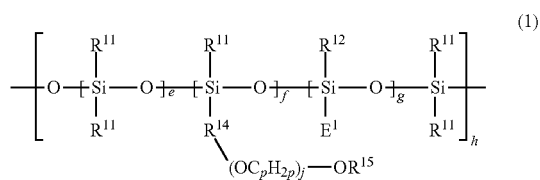

(1)

wherein $R^{11}$ represents a monovalent hydrocarbon group having 1 or more and 6 or less carbon atoms, $R^{12}$ represents any of $R^{11}$ or $E^1$, $E^1$ represents a monovalent group represented by —$R^{13}$—$Z^1$ (where $R^{13}$ represents a divalent hydrocarbon group having 1 or more and 6 or less carbon atoms, $Z^1$ represents a primary to tertiary amino group-containing group), $R^{14}$ represents a divalent hydrocarbon group having 1 or more and 6 or less carbon atoms, $R^{15}$ represents a hydrogen atom or a monovalent hydrocarbon group having 1 or more and 4 or less carbon atoms, e is a number of 1 or more and 50 or less, f is a number of 1 or more and 50 or less, g is a number of 1 or more and 50 or less, h is a number of 1 or more, j is a number of 2 or more and 100 or less, p is a number of 2 or more and 10 or less, the bonding order of the parenthesized structural units is not limited, and the bonding form thereof may be in a block form or a random form, j's (OC$_p$H$_{2p}$)s can be the same or different, plural $R^{11}$'s, $R^{12}$'s, $R^{14}$'s, $R^{15}$'s and $E^1$'s can be the same or different,

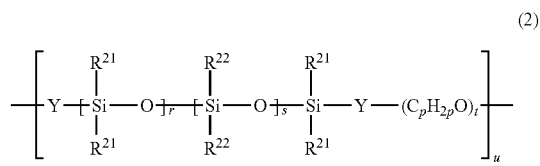

(2)

wherein $R^{21}$ represents a monovalent hydrocarbon group having 1 or more and 6 or less carbon atoms, $R^{22}$ represents any of $R^{21}$ or $E^2$, $E^2$ represents a monovalent group represented by —$R^{23}$—$Z^2$ (where $R^{23}$ represents a single bond, or a divalent hydrocarbon group having 1 or more and 20 or less carbon atoms, $Z^2$ represents a primary to tertiary amino group-containing group), Y represents a single bond, or a divalent group having 1 or more and 12 or less carbon atoms, in the case where all $R^{22}$'s are $R^{21}$'s, at least one Y is an amino group-containing divalent group, in the case where all Y's are divalent groups not containing an amino group, at least one $R^{22}$ is $E^2$, r is a number of 1 or more, s is a number of 1 or more, t is a number of 2 or more and 100 or less, u is a number of 1 or more, p is the same as above, and is a number of 2 or more and 10 or less, the bonding order of the parenthesized structural units is not limited, and the bonding form thereof may be in a block form or a random form, t's (C$_p$H$_{2p}$O)s can be the same or different, plural $R^{21}$'s, $R^{22}$'s, $E^2$'s and Y's can be the same or different.

<17>

The cosmetic composition according to <16>, wherein the component (B) is an aminopolyether-modified silicone (B2) having a repeating unit represented by the general formula (2).

<18>

The cosmetic composition according to <16>, wherein the component (B1) is an aminopolyether-modified silicone represented by the following general formula (1-1),

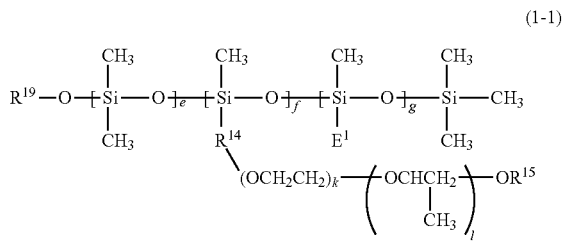

(1-1)

wherein $E^1$, $R^{14}$, $R^{15}$, e, f, and g are the same as above, $R^{19}$ represents a monovalent hydrocarbon group having 1 or more and 4 or less carbon atoms, or a trimethylsilyl group, k is a number of 1 or more and 50 or less, l is a number of 0 or more and 50 or less, and is preferably 1 or more and 50 or less.

<19>

The cosmetic composition according to any one of <16> to <18>, wherein the component (B2) is at least one selected from the group consisting of an aminopolyether-modified silicone having a structure represented by the following general formula (2-1) and an aminopolyether-modified silicone having a structure represented by the following general formula (2-2),

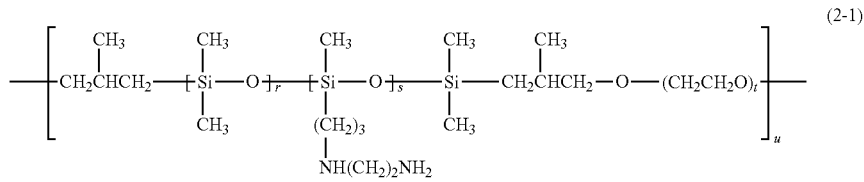

(2-1)

wherein r, s, t and u are the same as above,

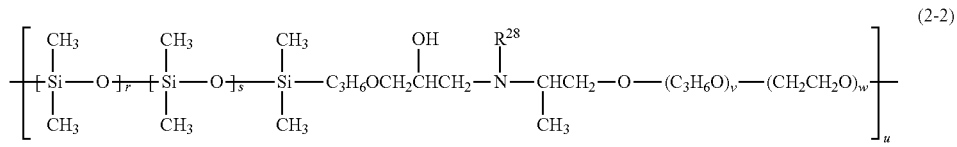

(2-2)

wherein $R^{28}$, r, s and u are the same as above, v is a number of 0 or more and 50 or less, preferably 2 or more and 50 or less, w is a number of 2 or more and 100 or less, v+w is a number of 4 or more and 100 or less, preferably a number of 4 or more and 80 or less, more preferably a number of 10 or more and 50 or less.

<20>

The cosmetic composition according to <19>, wherein the component (B2) is an aminopolyether-modified silicone having a structure represented by the general formula (2-1) or an aminopolyether-modified silicone having a structure represented by the general formula (2-2), more preferably an aminopolyether-modified silicone having a structure represented by the general formula (2-1).

<21>

The cosmetic composition according to any one of <1>, and <8> to <20>, wherein a ratio by mass of the component (B) to the component (A) in the cosmetic composition [(B)/(A)] is preferably 0.05 to 50, more preferably 0.10 to 15, even more preferably 0.10 to 8, further more preferably 0.17 to 5, further more preferably 0.17 to 3, further more preferably 0.17 to 2, further more preferably 0.20 to 1.

<22>

The cosmetic composition according to any one of <1>, and <8> to <21>, wherein the total content of the component (A) and the component (B) in the cosmetic composition is preferably 1 to 50% by mass, more preferably 2 to 25% by mass, even more preferably 3 to 20% by mass, further more preferably 3 to 18% by mass.

<23>

The cosmetic composition according to any one of <1> to <22>, wherein the content of the component (A) in the cosmetic composition is preferably 1 to 50% by mass, more preferably 1.5 to 35% by mass, even more preferably 1.5 to 20% by mass, further more preferably 2 to 15% by mass, further more preferably 3 to 15% by mass.

<24>

The cosmetic composition according to any one of <1> to <23>, wherein the content of the component (B) in the cosmetic composition is preferably 0.1 to 15% by mass, more preferably 0.2 to 10% by mass, even more preferably 0.5 to 8% by mass, further more preferably 0.5 to 5% by mass, further more preferably 0.5 to 3% by mass, further more preferably 1 to 3% by mass, further more preferably 1.3 to 3% by mass.

<25>

The cosmetic composition according to any one of <1> to <24>, wherein the content of water in the cosmetic composition is preferably 20% by mass or less, more preferably 10% by mass or less, even more preferably less than 5% by mass, further more preferably less than 2% by mass.

<26>

The cosmetic composition according to any one of <1> to <25>, further containing a solvent as a component (C).

<27>

The cosmetic composition according to <26>, wherein the component (C) contains at least one selected from the group consisting of dimethylpolysiloxane having a viscosity of 10 mm²/s or less at 25° C., methyltrimethicone, methylphenylpolysiloxane having a viscosity of 20 mm²/s or less , p at 25° C. entane, isopentane, hexane, isohexene, heptane, isoheptane, decane, isodecane, dodecane, isododecane, tetradecane, isotetradecane, tridecane, isotridecane, and light liquid isoparaffin, preferably at least one selected from the group consisting of dimethylpolysiloxane having a viscosity of 5 mm²/s or less , at 25° C. methyltrimethicone, isodecane, isododecane, isotetradecane and light liquid isoparaffin, more preferably at least one selected from the group consisting of isodecane, isododecane, isotetradecane and light liquid isoparaffin.

<28>

The cosmetic composition according to <26> or <27>, wherein the component (C) preferably contains a volatile alcohol solvent and at least one of a volatile hydrocarbon solvent or a volatile silicone solvent, more preferably contains at least one selected from the group consisting of ethanol, 1-propanol, 2-propanol, 1-butanol and 2-butanol, and at least one selected from the group consisting of dimethylpolysiloxane having a viscosity of 10 mm²/s or less at 25° C., methyltrimethicone, methylphenylpolysiloxane having a viscosity of 20 mm²/s or less at 25° C., pentane, isopentane, hexane, isohexene, heptane, isoheptane, decane, isodecane, dodecane, isododecane, tetradecane, isotetradecane, tridecane, isotridecane, and light liquid isoparaffin, even more preferably contains ethanol and at least one selected from the group consisting of dimethylpolysiloxane having a viscosity of 5 mm²/s or less at 25° C., methyltrimethicone, isodecane, isododecane, isotetradecane and light liquid isoparaffin, further more preferably contains ethanol and at least one selected from the group consisting of isodecane, isododecane, isotetradecane and light liquid isoparaffin.

<29>

The cosmetic composition according to any one of <26> to <28>, wherein the content of the component (C) in the cosmetic composition is preferably 40 to 98.9% by mass, more preferably 50 to 98.9% by mass, even more preferably 60 to 98% by mass.

<30>

The cosmetic composition according to any one of <1> to <29>, further containing a functional powder as a component (D).

<31>

The cosmetic composition according to <30>, wherein the content of the component (D) in the cosmetic composition is preferably 0.01 to 50% by mass, more preferably 0.1 to 50% by mass, even more preferably 0.2 to 30% by mass, further more preferably 0.3 to 30% by mass.

<32>

The cosmetic composition according to any one of <1> to <31>, which is a hair cosmetic composition.

<33>

The cosmetic composition according to any one of <1> to <31>, which is a hair dye composition.

<34>

A keratin substance treatment method including a step of applying the cosmetic composition of any one of <1> to <31> to a keratin substance and then drying it.

<35>

A hair treatment method including a step of applying the hair cosmetic composition of <32> to hair and then drying it.

<36>

A hair dyeing method including a step of applying the hair dye composition of <33> to hair and then drying it.

<37>

A leave-on cosmetic composition containing (A) a silicone film-forming agent and (B) an organopolysiloxane having a polyalkylene oxide moiety and a cationic group other than the component (A).

<38>

A leave-on cosmetic composition containing:
(A) a silicone film-forming agent, and
(B) an organopolysiloxane having a polyalkylene oxide moiety and a cationic group other than the component (A), wherein:
the total content of the component (A) and the component (B) in the cosmetic composition is 3% by mass or more and 18% by mass or less,
a ratio by mass of the component (B) to the component (A) in the cosmetic composition [(B)/(A)] is 0.17 or more and 5 or less.

<39>

A leave-on cosmetic composition containing:
(A) a silicone film-forming agent, and
(B) an organopolysiloxane having a polyalkylene oxide moiety and a cationic group other than the component (A), wherein:
the total content of the component (A) and the component (B) in the cosmetic composition is 3% by mass or more and 18% by mass or less,
a ratio by mass of the component (B) to the component (A) in the cosmetic composition [(B)/(A)] is 0.17 or more and 2 or less.

<40>

A leave-on cosmetic composition containing:
(A) 1 to 50% by mass of a silicone resin represented by an average formula, $(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains a Q unit represented by $SiO_{4/2}$ and an M unit represented by $(R^1)_3SiO_{1/2}$, and
(B) 0.1 to 15% by mass of an organopolysiloxane having a polyalkylene oxide moiety and a cationic group other than the component (A), in which the carbon number of the alkylene oxide constituting the polyalkylene oxide moiety is 1 to 6, the average addition molar number of the alkylene oxide is 2 to 100, and the cationic group is at least one selected from the group consisting of a primary amino group, a secondary amino group and a tertiary amino group, wherein:
the total content of the component (A) and the component (B) in the cosmetic composition is 3% by mass or more and 18% by mass or less,
a ratio by mass of the component (B) to the component (A) in the cosmetic composition [(B)/(A)] is 0.17 or more and 5 or less.

<41>

A leave-on cosmetic composition containing:
(A) 1 to 50% by mass of a silicone resin represented by an average formula, $(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains a Q unit represented by $SiO_{4/2}$ and an M unit represented by $(R^1)_3SiO_{1/2}$, and
(B) 0.1 to 15% by mass of an organopolysiloxane having a polyalkylene oxide moiety and a cationic group other than the component (A), in which the carbon number of the alkylene oxide constituting the polyalkylene oxide moiety is 1 to 6, the average addition molar number of the alkylene oxide is 2 to 100, and the cationic group is at least one selected from the group consisting of a primary amino group, a secondary amino group and a tertiary amino group, wherein:
the total content of the component (A) and the component (B) in the cosmetic composition is 3% by mass or more and 18% by mass or less,
a ratio by mass of the component (B) to the component (A) in the cosmetic composition [(B)/(A)] is 0.17 or more and 5 or less.

<42>

A leave-on cosmetic composition containing:
(A) 1 to 50% by mass of a silicone resin represented by $[SiO_{4/2}]_c[(R^1)_3SiO_{1/2}]_d$ wherein c and d each are an average repeating unit number and c>0 and d>0, and
(B) 0.1 to 15% by mass of an aminopolyether-modified silicone having a repeating unit represented by the following general formula (2),

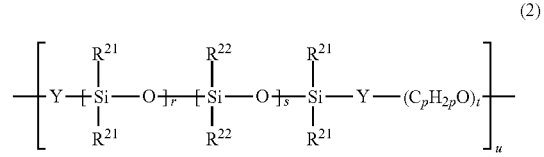

wherein R²¹ represents a monovalent hydrocarbon group having 1 or more and 6 or less carbon atoms, R²² represents any of R²¹ or E², E² represents a monovalent group represented by —R²³—Z² (where R²³ represents a single bond, or a divalent hydrocarbon group having 1 or more and 20 or less carbon atoms, Z² represents a primary to tertiary amino group-containing group), Y represents a single bond, or a divalent group having 1 or more and 12 or less carbon atoms, in the case where all R²²'s are R²¹'s, at least one Y is an amino group-containing divalent group, in the case where all Y's are divalent groups not containing an amino group, at least one R²² is E², r is a number of 1 or more, s is a number of 1 or more, t is a number of 2 or more and 100 or less, u is a number of 1 or more, p is the same as above, and is a number of 2 or more and 10 or less, the bonding order of the parenthesized structural units is not limited, and the bonding form thereof may be in a block form or a random form, t's $(C_pH_{2p}O)$s can be the same or different, plural R²¹'s, R²²'s, E²'s and Y's can be the same or different, wherein:

the total content of the component (A) and the component (B) in the cosmetic composition is 3% by mass or more and 18% by mass or less, a ratio by mass of the component (B) to the component (A) in the cosmetic composition [(B)/(A)] is 0.17 or more and 5 or less.

<43>
A leave-on cosmetic composition containing:
(A) 1 to 50% by mass of a silicone resin represented by $[SiO_{4/2}]_c[(R^1)_3SiO_{1/2}]_d$ wherein c and d each are an average repeating unit number and c>0 and d>0, and
(B) 0.1 to 15% by mass of an aminopolyether-modified silicone having a repeating unit represented by the following general formula (2),

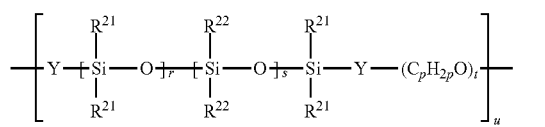
(2)

wherein R²¹ represents a monovalent hydrocarbon group having 1 or more and 6 or less carbon atoms, R²² represents any of R²¹ or E², E² represents a monovalent group represented by —R²³—Z² (where R²³ represents a single bond, or a divalent hydrocarbon group having 1 or more and 20 or less carbon atoms, Z² represents a primary to tertiary amino group-containing group), Y represents a single bond, or a divalent group having 1 or more and 12 or less carbon atoms, r is a number of 1 or more, s is a number of 1 or more, t is a number of 2 or more and 100 or less, u is a number of 1 or more, p is the same as above, and is a number of 2 or more and 10 or less, the bonding order of the parenthesized structural units is not limited, and the bonding form thereof may be in a block form or a random form, t's $(C_pH_{2p}O)$s can be the same or different, plural R²¹'s, R²²'s, E²'s and Y's can be the same or different, wherein:

the total content of the component (A) and the component (B) in the cosmetic composition is 3% by mass or more and 18% by mass or less, a ratio by mass of the component (B) to the component (A) in the cosmetic composition [(B)/(A)] is 0.17 or more and 2 or less.

<44>
A cosmetic kit provided with the following compositions (I) and (II):
(I) a composition containing (A) a silicone film-forming agent,
(II) a composition containing (B) an organopolysiloxane having a polyalkylene oxide moiety and a cationic group other than the component (A).

<45>
A cosmetic kit provided with the following compositions (I) and (II):
(I) a composition containing (A) a silicone film-forming agent,
(II) a composition containing (B) an organopolysiloxane having a polyalkylene oxide moiety and a cationic group other than the component (A), wherein:
the total content of the component (A) and the component (B) contained in the compositions (I) and (II) is 3% by mass or more and 18% by mass or less,
a ratio by mass of the component (B) to the component (A) contained in the compositions (I) and (II), [(B)/(A)] is 0.17 or more and 5 or less,
the content of water contained in the compositions (I) and (II) is 50% by mass or less.

<46>
A cosmetic kit provided with the following compositions (I) and (II):
(I) a composition containing (A) a silicone film-forming agent,
(II) a composition containing (B) an organopolysiloxane having a polyalkylene oxide moiety and a cationic group other than the component (A), wherein:
the total content of the component (A) and the component (B) contained in the compositions (I) and (II) is 3% by mass or more and 18% by mass or less,
a ratio by mass of the component (B) to the component (A) contained in the compositions (I) and (II), [(B)/(A)] is 0.17 or more and 2 or less,
the content of water contained in the compositions (I) and (II) is 50% by mass or less.

<47>
A cosmetic kit provided with the following compositions (I) and (II):
(I) a composition containing (A) a silicone resin represented by an average formula, $(R^1)_mSiO_{(4-m)/2}$ wherein R¹ represents a hydrocarbon group having 1 or more and 12 or less carbon atoms and optionally substituted with fluorine, or a hydroxy group, plural R¹'s can be the same as or different from each other, and m is an average number, representing a number of more than 0 and less than 3,
which contains a Q unit represented by $SiO_{4/2}$ and an M unit represented by $(R^1)_3SiO_{1/2}$, and
(II) a composition containing (B) an organopolysiloxane having a polyalkylene oxide moiety and a cationic group other than the component (A), in which the carbon number of the alkylene oxide constituting the polyalkylene oxide moiety is 1 to 6, the average addition molar number of the alkylene oxide is 2 to 100, and the cationic group is at least one selected from the group consisting of a primary amino group, a secondary amino group and a tertiary amino group, wherein:

the content of the component (A) contained in the compositions (I) and (II) is 1 to 50% by mass, the content of the component (B) therein is 0.1 to 15% by mass, the total content of the component (A) and the component (B) contained in the compositions (I) and (II) is 3% by mass or more and 18% by mass or less, a ratio by mass of the component (B) to the component (A) contained in the compositions (I) and (II), [(B)/(A)] is 0.17 or more and 5 or less, the content of water contained in the compositions (I) and (II) is 50% by mass or less.

<48>

A cosmetic kit provided with the following compositions (I) and (II):

(I) a composition containing (A) a silicone resin represented by an average formula, $(R^1)_m SiO_{(4-m)/2}$ wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3, which contains a Q unit represented by $SiO_{4/2}$ and an M unit represented by $(R^1)_3SiO_{1/2}$, and a composition containing (B) an organopolysiloxane having a polyalkylene oxide moiety and a cationic group other than the component (A), in which the carbon number of the alkylene oxide constituting the polyalkylene oxide moiety is 1 to 6, the average addition molar number of the alkylene oxide is 2 to 100, and the cationic group is at least one selected from the group consisting of a primary amino group, a secondary amino group and a tertiary amino group, wherein:

the content of the component (A) contained in the compositions (I) and (II) is 1 to 50% by mass, the content of the component (B) therein is 0.1 to 15% by mass, the total content of the component (A) and the component (B) contained in the compositions (I) and (II) is 3% by mass or more and 18% by mass or less, a ratio by mass of the component (B) to the component (A) contained in the compositions (I) and (II), [(B)/(A)] is 0.17 or more and 5 or less, the content of water contained in the compositions (I) and (II) is 50% by mass or less.

<49>

A cosmetic kit provided with the following compositions (I) and (II):

(I) a composition containing (A) a silicone resin represented by $[SiO_{4/2}]_c[(R^1)_3SiO_{1/2}]_d$ wherein c and d each are an average repeating unit number and c>0 and d>0, and a composition containing (B) an aminopolyether-modified silicone having a repeating unit represented by the following general formula (2),

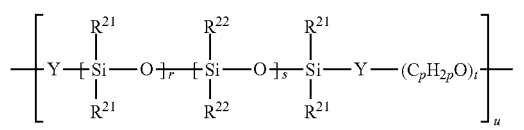

wherein $R^{21}$ represents a monovalent hydrocarbon group having 1 or more and 6 or less carbon atoms, $R^{22}$ represents any of $R^{21}$ or $E^2$, $E^2$ represents a monovalent group represented by $—R^{23}—Z^2$ (where $R^{23}$ represents a single bond, or a divalent hydrocarbon group having 1 or more and 20 or less carbon atoms, $Z^2$ represents a primary to tertiary amino group-containing group), Y represents a single bond, or a divalent group having 1 or more and 12 or less carbon atoms, in the case where all $R^{22}$'s are $R^{21}$'s, at least one Y is an amino group-containing divalent group, in the case where all Y's are divalent groups not containing an amino group, at least one $R^{22}$ is $E^2$, r is a number of 1 or more, s is a number of 1 or more, t is a number of 2 or more and 100 or less, u is a number of 1 or more, p is the same as above, and is a number of 2 or more and 10 or less, the bonding order of the parenthesized structural units is not limited, and the bonding form thereof may be in a block form or a random form, t's $(C_pH_{2p}O)$s can be the same or different, plural $R^{21}$'s, $R^{22}$'s, $E^2$'s and Y's can be the same or different, wherein:

the content of the component (A) contained in the compositions (I) and (II) is 1 to 50% by mass, the content of the component (B) therein is 0.1 to 15% by mass, the total content of the component (A) and the component (B) contained in the compositions (I) and (II) is 3% by mass or more and 18% by mass or less, a ratio by mass of the component (B) to the component (A) contained in the compositions (I) and (II), [(B)/(A)] is 0.17 or more and 5 or less, the content of water contained in the compositions (I) and (II) is 50% by mass or less.

<50>

A cosmetic kit provided with the following compositions (I) and (II):

(I) a composition containing (A) a silicone resin represented by $[SiO_{4/2}]_c[(R^1)_3SiO_{1/2}]_d$ wherein c and d each are an average repeating unit number and c>0 and d>0, and (II) a composition containing (B) an aminopolyether-modified silicone having a repeating unit represented by the following general formula (2),

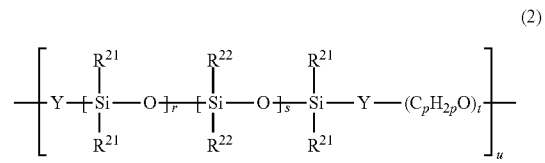

wherein $R^{21}$ represents a monovalent hydrocarbon group having 1 or more and 6 or less carbon atoms, $R^{22}$ represents any of $R^{21}$ or $E^2$, $E^2$ represents a monovalent group represented by $—R^{23}—Z^2$ (where $R^{23}$ represents a single bond, or a divalent hydrocarbon group having 1 or more and 20 or less carbon atoms, $Z^2$ represents a primary to tertiary amino group-containing group), Y represents a single bond, or a divalent group having 1 or more and 12 or less carbon atoms, in the case where all $R^{22}$'s are $R^{21}$'s, at least one Y is an amino group-containing divalent group, in the case where all Y's are divalent groups not containing an amino group, at least one $R^{22}$ is $E^2$, r is a number of 1 or more, s is a number of 1 or more, t is a number of 2 or more and 100 or less, u is a number of 1 or more, p is the same as above, and is a number of 2 or more and 10 or less, the bonding order of the parenthesized structural units is not limited, and the bonding form thereof may be in a block form or a random form, t's ($C_pH_{2p}O$)s can be the same or different, plural $R^{21}$'s, $R^{22}$'s, $E^2$'s and Y's can be the same or different, wherein:
the content of the component (A) contained in the compositions (I) and (II) is 1 to 50% by mass, the content of the component (B) therein is 0.1 to 15% by mass,
the total content of the component (A) and the component (B) contained in the compositions (I) and (II) is 3% by mass or more and 18% by mass or less,
a ratio by mass of the component (B) to the component (A) contained in the compositions (I) and (II), [(B)/(A)] is 0.17 or more and 2 or less,
the content of water contained in the compositions (I) and (II) is 50% by mass or less.

EXAMPLES

Hereinunder the present invention is described with reference to Examples, but the present invention is not restricted to the range of Examples. In these Examples, various measurements and evaluations were carried out according to the following methods.

<Preparation of Hair Bundles for Evaluation>

Human gray hair (100%) bundles (by Beaulax Co., Ltd., length 10 cm, mass 1 g) were shampooed with the following plain shampoo having a formulation mentioned below, then rinsed with warm water at 40° C., and fully dried to prepare hair bundles for evaluation.

Plain Shampoo Formulation

| Ingredient | (mass %) |
| --- | --- |
| Polyoxyethylene(2) lauryl ether sodium sulfate (*1) | 15.5 |
| Lauric acid diethanolamide (*2) | 1.5 |
| Tetrasodium edetate | 0.3 |
| Sodium benzoate | 1.43 |
| Pure water | balance |
| Total | 100.0 |

(*1): 57.4% by mass as Emal 227 (by Kao Corporation, active ingredient 27% by mass)
(*2): Aminon L-02 (by Kao Corporation)

<Feel After Treatment (Before Shampooing)ϕ
(Smoothness in Dry State)

0.2 g of the hair cosmetic composition of each Example was applied to the hair bundle for evaluation, and then this was dried for 1 minute with a drier ("P2-D250" by Hitachi Limited, setting HIGH) by applying hot air from a position separated by 18 cm from the hair bundle with combing, and thereafter still kept dried with hot air for 30 seconds for hair treatment. Expert panelists organoleptically evaluated the feel of the treated hair bundles according to the following criteria, and a total point of N=3 was calculated.

A total point of 4 or less means a non-smooth feel. A total point of 6 or more means a good feel, 8 or more means a better feel, and 11 or more means a further better feel.
4: Smooth feel.
3: Relatively smooth feel.
2: Slightly non-smooth feel.
1: Non-smooth feel.
(Smoothness in Rinsing)

0.2 g of the hair cosmetic composition of each Example was applied to the hair bundle for evaluation, and then this was dried for 1 minute with a drier ("P2-D250" by Hitachi Limited, setting HIGH) by applying hot air from a position separated by 18 cm from the hair bundle with combing, and thereafter still kept dried with hot air for 30 seconds for hair treatment. Expert panelists organoleptically evaluated the feel of the treated hair bundles in rinsing with hot water at about 40° C. according to the following criteria, and a total point of N=3 was calculated.

A total point of 4 or less means a non-smooth feel. A total point of 6 or more means a good feel, 8 or more means a better feel, and 11 or more means a further better feel.
4: Smooth feel.
3: Relatively smooth feel.
2: Slightly non-smooth feel.
1: Non-smooth feel.
<Feel After 7-time Shampooing>

The hair bundle treated in the same manner as above was shampooed with the plain shampoo having a formulation as above, rinsed with warm water at 40° C. and dried. The process was repeated 7 times. After shampooing 7 times, smoothness in a dry state and in rinsing was evaluated in the same manner as above.
<Shampooing Resistance (Difficulty of Discoloration in 7-time Shampooing)>

0.2 g of the hair cosmetic composition of Examples 2 to 8 was applied to the hair bundle for evaluation, and then this was dried for 1 minute with a drier ("P2-D250" by Hitachi Limited, setting HIGH) by applying hot air from a position separated by 18 cm from the hair bundle with combing, and thereafter still kept dried with hot air for 30 seconds for hair treatment.

The treated hair bundle was analyzed with a color difference meter (CR-400 by Konica Minolta, Inc.) in a CIE color system (L*,a*,b*). Then, this was shampooed with the plain shampoo having the formulation mentioned above, rinsed with warm water at 40° C. and dried. The process was repeated 7 times. After shampooing 7 times, the dried hair bundle was analyzed with the color difference meter in the same manner as above, and according to the following formulation, a color difference (ΔE*) from the hair bundle before shampooing was calculated. L*, a* and b* were measured at different 6 points on the hair bundle (each at 2 central points of each region obtained by equally dividing the hair bundle into three in the length direction), and the found data were averaged to give an average value.

$$\Delta E^* = \sqrt{(L_1^* - L_0^*)^2 + (a_1^* - a_0^*)^2 + (b_1^* - b_0^*)^2}$$

wherein:
$L_0^*$, $a_0^*$, $b_0^*$: found data of hair bundle before shampooing,
$L_1^*$, $a_1^*$, $b_1^*$: found data of hair bundle after 7-time shampooing
ΔE*<20 means that the treated hair is considered to have good shampooing resistance and to be excellent in color sustainability. ΔE*<15 means better, ΔE*<10 means even better and ΔE*<5 means further better.

Examples 1 to 8, Comparative Example 1
(Preparation and Evaluation of Hair Cosmetic Composition)

Ingredients shown in Tables 1 to 4 were blended according to the formulation described in each Table, and then mixed until uniform to prepare hair cosmetic compositions. The resultant hair cosmetic compositions were evaluated according to the above-mentioned methods. The results are shown in Tables 1 to 4.

The blending amount (mass %) shown in Tables is an active ingredient amount.

TABLE 1

| | (mass %) | | Example 1 | Comparative Example 1 |
|---|---|---|---|---|
| (A) | trimethylsiloxysilicate | X-21-5595 *1 | 7.5 | 7.5 |
| (B) | (bisisobutyl PEG-15/amodimethicone) copolymer | SS-3588 *2 | 1.5 | 1.5 |
| (D) | carbon black | DK BLACK No. 2 *3 | | |
| — | water | | | 80.0 |
| (C) | isododecane | Marukasol R *4 | balance | balance |
| | Total | | 100 | 100 |
| Total content (mass %) (A) + (B) | | | 9.0 | 9.0 |
| Ratio by mass (B)/(A) | | | 0.20 | 0.20 |
| Evaluation Results | Feel after treatment (before shampooing) | Smoothness in dry state | 9 | * |
| | | Smoothness in rinsing | 8 | * |
| | Feel after 7-time shampooing | Smoothness in dry state | 10 | * |
| | | Smoothness in rinsing | 8 | * |

* Evaluation impossible owing to precipitation

TABLE 2

| | (mass %) | | Example 2 | Example 3 | Example 4 | Example 5 |
|---|---|---|---|---|---|---|
| (A) | trimethylsiloxysilicate | X-21-5595 *1 | 7.8 | 7.5 | 4.5 | 1.5 |
| (B) | (bisisobutyl PEG-15/amodimethicone) copolymer | SS-3588 *2 | 1.2 | 1.5 | 4.5 | 7.5 |
| (D) | carbon black | DK BLACK No. 2 *3 | 1.5 | 1.5 | 1.5 | 1.5 |
| (C) | isododecane | Marukasol R *4 | balance | balance | balance | balance |
| | Total | | 100 | 100 | 100 | 100 |
| | Total content (mass %) (A) + (B) | | 9.0 | 9.0 | 9.0 | 9.0 |
| | Ratio by mass (B)/(A) | | 0.15 | 0.20 | 1.00 | 5.00 |
| Evaluation Results | Feel after treatment (before shampooing) | Smoothness in dry state | 8 | 9 | 10 | 11 |
| | | Smoothness in rinsing | 7 | 8 | 10 | 12 |
| | Feel after 7-time shampooing | Smoothness in dry state | 8 | 10 | 10 | 11 |
| | | Smoothness in rinsing | 7 | 8 | 11 | 12 |
| | Shampooing resistance (difficulty of discoloration by shampooing) | ΔE* after 7-time shampooing | 7.2 | 4.6 | 2.9 | 5.4 |

TABLE 3

| | (mass %) | | Example 6 | Example 3 | Example 7 |
|---|---|---|---|---|---|
| (A) | trimethylsiloxysilicate | X-21-5595 *1 | 1.667 | 7.5 | 16.67 |
| (B) | (bisisobutyl PEG-15/amodimethicone) copolymer | SS-3588 *2 | 0.333 | 1.5 | 3.33 |
| (D) | carbon black | DK BLACK No. 2 *3 | 1.5 | 1.5 | 1.5 |
| (C) | isododecane | Marukasol R *4 | balance | balance | balance |
| | Total | | 100 | 100 | 100 |
| Total content (mass %) (A) + (B) | | | 2.0 | 9.0 | 20.0 |
| Ratio by mass (B)/(A) | | | 0.20 | 0.20 | 0.20 |
| Evaluation Results | Feel after treatment (before shampooing) | Smoothness in dry state | 10 | 9 | 8 |
| | | Smoothness in rinsing | 6 | 8 | 7 |

TABLE 3-continued

| (mass %) | | Example 6 | Example 3 | Example 7 |
|---|---|---|---|---|
| Feel after 7-time shampooing | Smoothness in dry state | 9 | 10 | 8 |
| | Smoothness in rinsing | 6 | 8 | 7 |
| Shampooing resistance (difficulty of discoloration by shampooing) | ΔE* after 7-time shampooing | 13.8 | 4.6 | 14.2 |

TABLE 4

| | (Kind) | (Material Name) | Example 3 | Example 8 |
|---|---|---|---|---|
| (A) | trimethylsiloxysilicate | X-21-5595 *1 | 7.5 | |
| | polypropylsilsesquioxane | 680 Fluid *5 | | 7.5 |
| (B) | (bisisobutyl PEG-15/amodimethicone) copolymer | SS-3588 *2 | 1.5 | 1.5 |
| (D) | carbon black | DK BLACK No. 2 *3 | 1.5 | 1.5 |
| (C) | isododecane | Marukasol R *4 | balance | balance |
| | Total | | 100 | 100 |
| Total content (mass %) (A) + (B) | | | 9.0 | 9.0 |
| Ratio by mass (B)/(A) | | | 0.20 | 0.20 |
| Evaluation Results | Feel after treatment (before shampooing) | Smoothness in dry state | 9 | 12 |
| | | Smoothness in rinsing | 8 | 7 |
| | Feel after 7-time shampooing | Smoothness in dry state | 10 | 10 |
| | | Smoothness in rinsing | 8 | 7 |
| | Shampooing resistance (difficulty of discoloration by shampooing) | ΔE* after 7-time shampooing | 4.6 | 17.8 |

Components shown in Tables are as follows.
*1: X-21-5595, by Shin-Etsu Chemical Industry Co., Ltd., isododecane solution of trimethylsiloxysilicate (60 mass %)
*2: DOWSIL SS-3588 Fluid, by Dow Toray Corporation, (bisisobutyl PEG-15/amodimethicone) copolymer
*3: DK BLACK No. 2, by Daito Kasei Kogyo Co., Ltd., carbon black
*4: Marukasol R, by Maruzen Petrochemical Co., Ltd., isododecane
*5: DOWSIL 680 ID Fluid, by Dow Toray Corporation, isododecane solution of polypropylsilsesquioxane (75% by mass)

From Table 1, it is known that when the cosmetic composition of the present invention is applied to dry hair in leave-on use, it can impart thereto a smooth feel in a dry state and in rinsing, and in addition, even after shampooing, these effects are sustained excellently. Also as shown in Tables 2 to 4, it is known that, in the case where the cosmetic composition containing a pigment is used as a hair dye composition, the above-mentioned effects can be given to hair and the color consistency is also good with little fading by shampooing.

Industrial Applicability

According to the present invention, there can be provided a cosmetic composition which is, when applied to a keratin substance such as skin or hair in a dry state and especially when used without rinsing away with water, able to impart a smooth feel in a dry state or in rinsing, and is, even after washing, able to be excellent in sustainability of these effects. In addition, when the cosmetic composition is used as a hair dye composition, it can impart the above-mentioned effects to hair and secure good color consistency with little fading by shampooing.

The invention claimed is:

1. A cosmetic composition comprising:
   (A) a silicone film-forming agent, and
   (B) an organopolysiloxane having a polyalkylene oxide moiety and a cationic group other than the component (A), wherein:
   the content of water is 1% by mass or less, and
   a ratio by mass of the component (B) to the component (A) is 0.17 or more and 5 or less.

2. The cosmetic composition according to claim 1, wherein the component (A) is at least one selected from the group consisting of the following components (A1) and (A2):
   (A1) a silicone resin represented by an average formula, $(R^1)_m SiO_{(4-m)/2}$
   wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
   which contains at least one unit selected from the group consisting of a T unit represented by $R^1SiO_{3/2}$ and a Q unit represented by $SiO_{4/2}$, (A2) a silicone polymer containing a polysiloxane moiety and a moiety formed of a non-silicone organic chain.

3. The cosmetic composition according to claim 2, wherein the component (A2) contains an acrylsilicone polymer (A2-1).

4. The cosmetic composition according to claim 1, wherein an alkylene oxide constituting the polyalkylene oxide moiety of the component (B) is at least one selected from ethylene oxide and propylene oxide.

5. The cosmetic composition according to claim 1, wherein a content of the component (A) is 1% by mass or more and 50% by mass or less.

6. The cosmetic composition according to claim 1, further containing a solvent as a component (C).

7. The cosmetic composition according to claim 1, further containing a functional powder as a component (D).

8. The cosmetic composition according to claim 1, which is a hair cosmetic composition.

9. The cosmetic composition according to claim 1, which is a hair dye composition.

10. A method for treating a keratin substance, comprising applying the cosmetic composition of claim 1 to the keratin substance and then drying it.

11. A method for treating hair, comprising applying the hair cosmetic composition of claim 8 to the hair and then drying it.

12. A method for dyeing hair, comprising applying the hair dye composition of claim 9 to the hair and then drying it.

13. A leave-on cosmetic composition comprising (A) a silicone film-forming agent, and (B) an organopolysiloxane having a polyalkylene oxide moiety and a cationic group other than the component (A), wherein:
- the leave-on cosmetic composition has a content of water of 1% by mass or less, and
- a ratio by mass of the component (B) to the component (A) is 0 17 or more and 5 or less.

14. A cosmetic kit, comprising compositions (I) and (II):
(I) a composition containing (A) a silicone film-forming agent,
(II) a composition containing (B) an organopolysiloxane having a polyalkylene oxide moiety and a cationic group other than the component (A),
provided that a ratio by mass of the component (B) to the component (A) is 0.17 or more and 5 or less, and
wherein a total content of water in the compositions (I) and (II) is 1% by mass or less.

* * * * *